US010290157B2

(12) United States Patent
Nijlunsing et al.

(10) Patent No.: US 10,290,157 B2
(45) Date of Patent: May 14, 2019

(54) INTERACTIVE PLACEMENT OF ANATOMICAL ATLAS STRUCTURES IN PATIENT IMAGES

(71) Applicant: Medtronic Bakken Research Center B.V., Maastricht (NL)

(72) Inventors: Rutger Nijlunsing, Veldhoven (NL); Stefan Marien, Eindhoven (NL)

(73) Assignee: Medtronic Bakken Research Center B.V., Maastricht (NL)

( * ) Notice: Subject to any disclaimer, the term of this patent is extended or adjusted under 35 U.S.C. 154(b) by 0 days.

(21) Appl. No.: 15/625,414

(22) Filed: Jun. 16, 2017

(65) Prior Publication Data

US 2017/0365103 A1   Dec. 21, 2017

Related U.S. Application Data

(60) Provisional application No. 62/351,574, filed on Jun. 17, 2016, provisional application No. 62/366,999, filed on Jul. 26, 2016.

(51) Int. Cl.
*A61N 1/00* (2006.01)
*G06T 19/20* (2011.01)
(Continued)

(52) U.S. Cl.
CPC ............ *G06T 19/20* (2013.01); *A61B 5/0478* (2013.01); *A61B 5/6868* (2013.01);
(Continued)

(58) Field of Classification Search
CPC ......... G06T 19/20; G06T 7/30; A61N 1/3605; A61N 1/0534; A61N 1/36128;
(Continued)

(56) References Cited

U.S. PATENT DOCUMENTS 8,958,615 B2    2/2015  Blum et al.
9,308,372 B2    4/2016  Sparks et al.
(Continued)

FOREIGN PATENT DOCUMENTS

EP         2691900 A2    2/2014
WO     2012135198 A1   10/2012

OTHER PUBLICATIONS

International Search Report and Written Opinion from International Application No. PCT/EP2017/064829, dated Sep. 9, 2017, 14 pp.

*Primary Examiner* — Scott M. Getzow
(74) *Attorney, Agent, or Firm* — Shumaker & Sieffert, P.A.

(57) ABSTRACT

This disclosure describes systems, devices, and techniques for adjusting an anatomical atlas to patient anatomy. In one example, a system may include processing circuitry configured to generate, for display at a user interface, a representation of an anatomical region of a patient, generate, for display at the user interface, a representation of one or more atlas-defined anatomical structures at a first position over the representation of the anatomical region of the patient, receive a user annotation that defines an adjustment to at least one atlas-defined anatomical structure relative to the representation of the anatomical region of the patient, and adjust, based on the adjustment, the first position of the representation of the one or more atlas-defined anatomical structures to a second position of the representation of the one or more atlas-defined anatomical structures over the representation of the anatomical region of the patient.

25 Claims, 15 Drawing Sheets

(51) Int. Cl.
*A61N 1/05* (2006.01)
*A61N 1/36* (2006.01)
*A61N 1/372* (2006.01)
*A61B 5/00* (2006.01)
*A61B 5/0478* (2006.01)
*G06T 7/30* (2017.01)
*G06F 3/0486* (2013.01)
*A61B 90/00* (2016.01)

(52) U.S. Cl.
CPC ......... *A61N 1/0534* (2013.01); *A61N 1/3605* (2013.01); *A61N 1/36128* (2013.01); *A61N 1/37247* (2013.01); *G06T 7/30* (2017.01); *A61B 2090/364* (2016.02); *A61B 2576/026* (2013.01); *A61N 1/36003* (2013.01); *A61N 1/36007* (2013.01); *A61N 1/36062* (2017.08); *A61N 1/36064* (2013.01); *A61N 1/36067* (2013.01); *A61N 1/36071* (2013.01); *A61N 1/36085* (2013.01); *A61N 1/36107* (2013.01); *A61N 1/36185* (2013.01); *G06F 3/0486* (2013.01); *G06T 2210/41* (2013.01); *G06T 2219/004* (2013.01); *G06T 2219/028* (2013.01); *G06T 2219/2016* (2013.01)

(58) Field of Classification Search
CPC ............ A61N 1/37247; A61N 1/36067; A61N 1/36064; A61N 1/36062; A61N 1/36007; A61N 1/36185; A61N 1/36107; A61B 5/0478; A61B 5/6868; A61B 2090/364; A61B 2576/026
See application file for complete search history.

(56) References Cited

U.S. PATENT DOCUMENTS

| | | | |
|---|---|---|---|
| 9,314,305 B2 | 4/2016 | Jenkins et al. | |
| 2007/0203545 A1* | 8/2007 | Stone | A61N 1/0529 607/59 |
| 2007/0203546 A1 | 8/2007 | Stone et al. | |
| 2009/0287271 A1 | 11/2009 | Blum et al. | |
| 2011/0264165 A1 | 10/2011 | Molnar et al. | |
| 2012/0265268 A1 | 10/2012 | Blum et al. | |
| 2013/0039550 A1* | 2/2013 | Blum | G06T 7/0014 382/128 |
| 2014/0316248 A1 | 10/2014 | Decharms | |

* cited by examiner

INTERACTIVE PLACEMENT OF ANATOMICAL ATLAS STRUCTURES IN PATIENT IMAGES

This application claims the benefit of U.S. Provisional Patent Application No. 62/351,574 by Nijlunsing et al., entitled "INTERACTIVE PLACEMENT OF ANATOMICAL ATLAS STRUCTURES IN PATIENT IMAGES," filed Jun. 17, 2016 and U.S. Provisional Patent Application No. 62/366,999 by Nijlunsing et al., entitled "INTERACTIVE PLACEMENT OF ANATOMICAL ATLAS STRUCTURES IN PATIENT IMAGES," filed Jul. 26, 2016. The entire contents of Application Nos. 62/351,574 and 62/366,999 are incorporated herein by reference.

TECHNICAL FIELD

This disclosure generally relates to medical devices, and more specifically, to user interfaces for placing anatomical atlases with respect to representations of anatomical regions of a patient.

BACKGROUND

Implantable electrical stimulators may be used to deliver electrical stimulation therapy to patients to treat a variety of symptoms or conditions such as chronic pain, tremor, Parkinson's disease, epilepsy, urinary or fecal incontinence, sexual dysfunction, obesity, or gastroparesis. In general, an implantable stimulator delivers neurostimulation therapy in the form of electrical pulses. An implantable stimulator may deliver neurostimulation therapy via one or more leads that include electrodes located proximate to target tissues of the brain, the spinal cord, pelvic nerves, peripheral nerves, or the stomach of a patient. Hence, stimulation may be used in different therapeutic applications, such as deep brain stimulation (DBS), spinal cord stimulation (SCS), pelvic stimulation, gastric stimulation, or peripheral nerve stimulation. Stimulation also may be used for muscle stimulation, e.g., functional electrical stimulation (FES) to promote muscle movement or prevent atrophy.

In general, a clinician selects values for a number of programmable parameters in order to define the electrical stimulation therapy to be delivered by the implantable stimulator to a patient. For example, the clinician ordinarily selects a combination of electrodes carried by one or more implantable leads, and assigns polarities to the selected electrodes. In addition, the clinician selects an amplitude, which may be a current or voltage amplitude, a pulse width and a pulse rate for stimulation pulses to be delivered to the patient. A group of parameters, including electrode combination, electrode polarity, amplitude, pulse width and pulse rate, may be referred to as a program in the sense that they drive the neurostimulation therapy to be delivered to the patient. In some applications, an implantable stimulator may deliver stimulation therapy according to multiple programs either simultaneously or on a time-interleaved, overlapping or non-overlapping, basis.

The process of selecting electrode combinations and other parameters can be time consuming, and may require a great deal of trial and error before a therapeutic program is discovered. The "best" program may be a program that best balances greater clinical efficacy and minimal side effects experienced by the patient. In addition, some programs may consume less power during therapy. The clinician typically needs to test a large number of possible electrode combinations within the electrode set implanted in the patient, in order to identify an optimal combination of electrodes and associated polarities. As mentioned previously, an electrode combination is a selected subset of one or more electrodes located on one or more implantable leads coupled to an implantable neurostimulator. As a portion of the overall parameter selection process, the process of selecting electrodes and the polarities of the electrodes can be particularly time-consuming and tedious.

The clinician may test electrode combinations by manually specifying combinations based on intuition or some idiosyncratic methodology. The clinician may then record notes on the efficacy and side effects of each combination after delivery of stimulation via that combination. In some cases, efficacy can be observed immediately within the clinic. For example, spinal cord stimulation may produce paresthesia and side effects that can be observed by the clinician based on patient feedback. In other cases, side effects and efficacy may not be apparent until a program has been applied for an extended period of time, as is sometimes the case in deep brain stimulation. Upon receipt of patient feedback and/or observation of symptoms by the clinician, the clinician is able to compare and select from the tested programs.

In order to improve the efficacy of neurostimulation therapy, electrical stimulators have grown in capability and complexity. Modern neurostimulators tend to have larger numbers of electrodes and potential electrode combinations, larger parameter ranges, and the ability to simultaneously deliver multiple therapy configurations by interleaving stimulation pulses in time. Although these factors increase the clinician's ability to adjust therapy for a particular patient or disease state, the burden involved in optimizing the device parameters has similarly increased. Unfortunately, fixed reimbursement schedules and scarce clinic time present challenges to effective programming of neurostimulator therapy.

SUMMARY

In general, this disclosure describes devices, systems and techniques that facilitate user adjustment of the position of one or more structure of an anatomical atlas to patient anatomy. A system, or the clinician, may use the anatomical atlas for configuring electrical stimulation therapy for the patient, in some examples. The atlas is a reference anatomical region of a reference anatomy that can be used to identify structures of a patient anatomy, e.g., structures that a clinician desires to stimulate for therapy. One or more leads having a complex electrode array geometry may be configured to deliver a stimulation field intended to affect, or avoid, one or more structures identified by the anatomical atlas. The techniques may be applied to a programming interface associated with a clinician programmer, a patient programmer, or both.

A system may receive one or more images of patient anatomy and present at least a portion of an anatomical atlas over the representation of the patient anatomy. Since the system may not automatically align the structures of the anatomical atlas correctly with the structures of the patient anatomy illustrated in the representation, the system may receive, via a user interface, a user annotation that indicates a location with respect to the patient anatomy at which the atlas structure should be located. For example, the user may provide input one in one or more views of the patient image that indicates where a structure of the atlas should be located with respect to the patient image. Based on the user annotation, the system may adjust the position of one or more structures of the anatomical atlas to more closely align with the patient anatomy. The system may then use the adjusted anatomical atlas to indicate structures of patient anatomy that can be used when determining stimulation parameters that define subsequent electrical stimulation therapy.

In one example, this disclosure describes a method including: generating, by one or more processors and for display at a user interface, a representation of an anatomical region of a patient; generating, by the one or more processors and for display at the user interface, a representation of one or more atlas-defined anatomical structures at a first position over the representation of the anatomical region of the patient; receiving, by the one or more processors, a user annotation that defines an adjustment to at least one atlas-defined anatomical structure of the one or more atlas-defined anatomical structures relative to the representation of the anatomical region of the patient; adjusting, by the one or more processors and based on the adjustment defined by the user annotation, the first position of the representation of the one or more atlas-defined anatomical structures to a second position of the representation of the one or more atlas-defined anatomical structures over the representation of the anatomical region of the patient; and controlling, by the one or more processors, the user interface to display the representation of the one or more atlas-defined anatomical structures at the second position over the representation of the anatomical region of the patient.

In another example, this disclosure describes a system, including: processing circuitry configured to: generate, for display at a user interface, a representation of an anatomical region of a patient; generate, for display at the user interface, a representation of one or more atlas-defined anatomical structures at a first position over the representation of the anatomical region of the patient; receive a user annotation that defines an adjustment to at least one atlas-defined anatomical structure of the one or more atlas-defined anatomical structures relative to the representation of the anatomical region of the patient; adjust, based on the adjustment defined by the user annotation, the first position of the representation of the one or more atlas-defined anatomical structures to a second position of the representation of the one or more atlas-defined anatomical structures over the representation of the anatomical region of the patient; and control the user interface to display the representation of the one or more atlas-defined anatomical structures at the second position over the representation of the anatomical region of the patient.

In another example, this disclosure describes a non-transitory computer readable medium including instructions that, when executed, cause at least one processor to: generate, for display at a user interface, a representation of an anatomical region of a patient; generate, for display at the user interface, a representation of one or more atlas-defined anatomical structures at a first position over the representation of the anatomical region of the patient; receive a user annotation that defines an adjustment to at least one atlas-defined anatomical structure of the one or more atlas-defined anatomical structures relative to the representation of the anatomical region of the patient; adjust, based on the adjustment defined by the user annotation, the first position of the representation of the one or more atlas-defined anatomical structures to a second position of the representation of the one or more atlas-defined anatomical structures over the representation of the anatomical region of the patient; and control the user interface to display the representation of the one or more atlas-defined anatomical structures at the second position over the representation of the anatomical region of the patient.

The details of one or more examples of the techniques of this disclosure are set forth in the accompanying drawings and the description below. Other features, objects, and advantages of the techniques will be apparent from the description and drawings, and from the claims.

DETAILED DESCRIPTION

Figure 1:
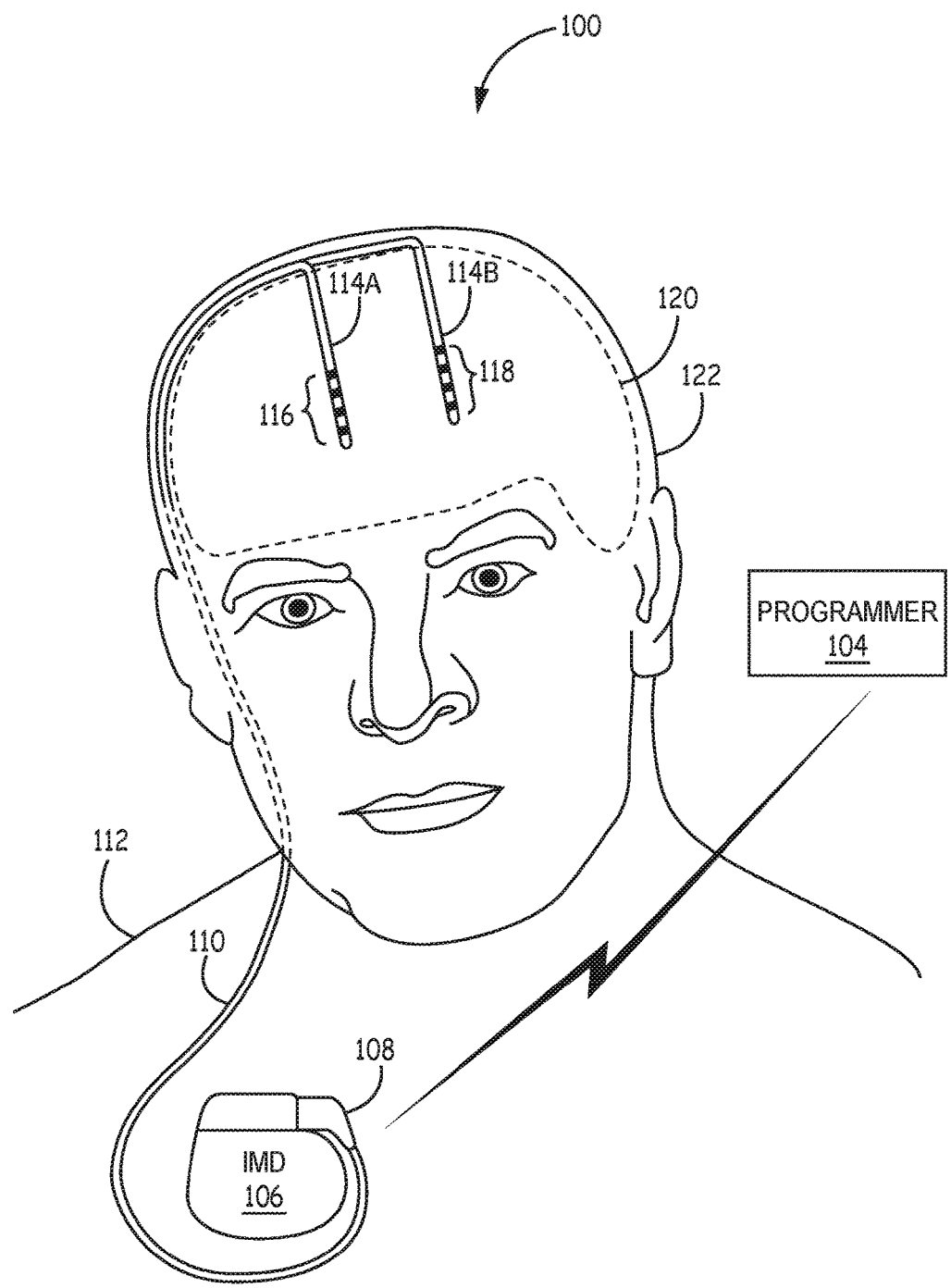
FIG. 1 is a conceptual diagram illustrating an example system that includes an implantable medical device (IMD) configured to deliver deep brain stimulation to a patient.

As described herein, systems, devices, and techniques facilitate adjustment of the position of one or more structures of an anatomical atlas to correspond with patient anatomy. The task of effectively configuring electrical stimulation therapy to treat a patient increases substantially as geometries and capabilities of stimulation leads become more complex. In particular, leads with complex electrode array geometries present the difficult task of selecting appropriate electrodes of a lead to target one or more anatomical structures of the patient intended to be targeted by a clinician. A clinician may use an atlas, or a reference anatomical region of a reference anatomy, to identify structures of the patient anatomy to stimulate for therapy. In some examples, a clinician overlays a representative structure of an atlas over a representation of the patient anatomy to identify areas of the patient anatomy to target for therapy. Allowing the clinician to partially or completely disregard the electrode locations and focus on selecting the structures that need to be stimulated to treat the patient may decrease clinician time programming therapy, simplify the task of electrode and stimulation parameter selection for the electrical stimulation, and increase the resulting therapy efficacy. Based upon the selected anatomical structures, the system may automatically generate stimulation parameters for efficacious therapy.

In some cases, a lead icon representing the implanted lead is displayed with the atlas and/or an image of the patient anatomy to show the clinician where the lead is relative to one or more anatomical regions of the atlas and/or patient anatomy. Electrodes mounted at different axial and angular positions of an implanted lead may allow the clinician to provide a more directional stimulation field to more effectively stimulate a target nerve site, reduce side effects, and/or compensate for inaccurate lead placement.

Anatomical structure selection via an anatomical atlas may be efficient for clinician programming and allow the system to generate stimulation parameters that are effectively to treat the patient. In some examples, an image of the actual patient anatomical region is presented over the atlas. However, since the atlas may not correspond exactly to the patient anatomy, anatomical structures indicated by the atlas may not accurately represent the same anatomical structure of the patient anatomy. Selecting structures from the atlas may thus not provide the most accurate basis for the determination of stimulation parameters and electrode combinations due to these differences between the atlas and the patient anatomical region approximated by the atlas. In other words, therapy based on anatomical structures indicated by an inaccurate atlas may not effectively treat the patient's condition and/or cause undesirable side effect.

Accordingly, the techniques of the disclosure allow for a user to provide an annotation that indicates the actual position of the anatomical structures in an atlas with respect to the same anatomical structures of the patient. The system of the disclosure receives the annotation and adjusts the position of one or more structures of the anatomical region represented by the atlas to more closely align with the actual position of the same anatomical structures of the patient. After adjusting the structures defined by the atlas, the system may select appropriate stimulation parameters to target the selected anatomical structures indicated by the corrected atlas and control delivery of electrical stimulation to the patient using the selected stimulation parameters.

The disclosure describes multiple examples of a user interface designed to receive user input, such as from a clinician, that corrects the location of one or more anatomical structures of an atlas to patient anatomy. For example, a system may receive user input that is an annotation defining one or more adjustments to one or more structures of the atlas that would more closely align, or match, the anatomy of the specific patient in question. This user annotation may indicate a different location of the structure and/or different shapes or sizes of the structure that would more closely align the structure to the actual structure represented in the patient's anatomy. The user annotation may be received via one or more two-dimensional (2D) views (e.g., different orthogonal views) of the representation of the atlas and patient anatomy to simplify the user input required. Based on the annotations in one or more 2D views, the system may translate or rotate the one or more atlas-defined anatomical structures in three dimensions. In some examples, the adjusted atlas-defined anatomical structures may not exactly match the user annotations and/or the patient anatomy, but the adjusted atlas-defined anatomical structures may provide a much more accurate correlation between the atlas-defined anatomical structures and the patient anatomy.

A user may then use the adjusted atlas to identify structures within the patient anatomy and efficiently program delivery of stimulation from leads having complex electrode array geometries. For example, the user interface may use a 3D environment to display the anatomical structures of the atlas and/or patient anatomy and a proposed stimulation field. This visual representation may allow a clinician to more effectively visualize and efficiently program electrical stimulation from complex lead geometries to target the desired anatomical structures than would be possible using an atlas that does not correlate with the patient anatomy. In other words, the adjusted atlas described herein may reduce the number of corrections to stimulation therapy before effective stimulation parameters and electrode combinations are determined for the patient.

FIG. 1 is a conceptual diagram illustrating an example system 100 that includes an implantable medical device (IMD) 106 configured to deliver deep brain stimulation to a patient 112. According to the techniques of the disclosure, a clinician targets an anatomical region of brain 120 of patient 112 for stimulation therapy. The clinician selects the targeted region based on a structure defined an atlas and adjusted according to an annotation provided by a clinician.

System 100 may be configured to treat a patient condition, such as a movement disorder, neurodegenerative impairment, a mood disorder or a seizure disorder of patient 112. Patient 112 ordinarily will be a human patient. In some cases, however, therapy system 100 may be applied to other mammalian or non-mammalian, non-human patients. While movement disorders and neurodegenerative impairment are primarily referred to herein, in other examples, therapy system 100 may provide therapy to manage symptoms of other patient conditions, such as, but not limited to, seizure disorders (e.g., epilepsy) or mood (or psychological) disorders (e.g., major depressive disorder (MDD), bipolar disorder, anxiety disorders, post-traumatic stress disorder, dysthymic disorder, and obsessive-compulsive disorder (OCD)). At least some of these disorders may be manifested in one or more patient movement behaviors. As described herein, a movement disorder or other neurodegenerative impairment may include symptoms such as, for example, muscle control impairment, motion impairment or other movement problems, such as rigidity, spasticity, bradykinesia, rhythmic hyperkinesia, nonrhythmic hyperkinesia, and akinesia. In some cases, the movement disorder may be a symptom of Parkinson's disease. However, the movement disorder may be attributable to other patient conditions.

Example therapy system 100 includes medical device programmer 104, implantable medical device (IMD) 106, lead extension 110, and leads 114A and 114B with respective sets of electrodes 116, 118. In the example shown in FIG. 1, electrodes 116, 118 of leads 114A, 114B are positioned to deliver electrical stimulation to a tissue site within brain 120, such as a deep brain site under the dura mater of brain 120 of patient 112. In some examples, delivery of stimulation to one or more regions of brain 120, such as the subthalamic nucleus, globus pallidus or thalamus, may be an effective treatment to manage movement disorders, such as Parkinson's disease. Electrodes 116, 118 are also positioned to sense bioelectrical brain signals within brain 120 of patient 112. In some examples, some of electrodes 116, 118 may be configured to sense bioelectrical brain signals and others of electrodes 116, 118 may be configured to deliver electrical stimulation to brain 120. In other examples, all of electrodes 116, 118 are configured to both sense bioelectrical brain signals and deliver electrical stimulation to brain 120.

IMD 106 includes a therapy module (e.g., which may include processing circuitry or other electrical circuitry configured to perform the functions attributed to IMD 106) that includes a stimulation generator configured to generate and deliver electrical stimulation therapy to patient 112 via a subset of electrodes 116, 118 of leads 114A and 114B, respectively. The subset of electrodes 116, 118 that are used to deliver electrical stimulation to patient 112, and, in some cases, the polarity of the subset of electrodes 116, 118, may be referred to as a stimulation electrode combination. As described in further detail below, the stimulation electrode combination can be selected for a particular patient 112 and target tissue site (e.g., selected based on the patient condition). The group of electrodes 116, 118 includes at least one electrode and can include a plurality of electrodes. In some examples, the plurality of electrodes 116 and/or 118 may have a complex electrode geometry such that two or more electrodes are located at different positions around the perimeter of the respective lead. In some examples, the bioelectrical signals sensed within brain 120 may reflect changes in electrical current produced by the sum of electrical potential differences across brain tissue. Examples of bioelectrical brain signals include, but are not limited to, electrical signals generated from local field potentials (LFP) sensed within one or more regions of brain 120, such as an electroencephalogram (EEG) signal, or an electrocorticogram (ECoG) signal. Local field potentials, however, may include a broader genus of electrical signals within brain 120 of patient 112. Each of these signals may be correlated or calibrated with the identified patient behavior and used for feedback in controlling the delivery of therapy.

In some examples, the bioelectrical brain signals that are used to select a stimulation electrode combination may be sensed within the same region of brain 120 as the target tissue site for the electrical stimulation. As previously indicated, these tissue sites may include tissue sites within anatomical structures such as the thalamus, subthalamic nucleus or globus pallidus of brain 120, as well as other target tissue sites. The specific target tissue sites and/or regions within brain 120 may be selected based on the patient condition. Thus, in some examples, both a stimulation electrode combination and sense electrode combinations may be selected from the same set of electrodes 116, 118. In other examples, the electrodes used for delivering electrical stimulation may be different than the electrodes used for sensing bioelectrical brain signals.

Electrical stimulation generated by IMD 106 may be configured to manage a variety of disorders and conditions. In some examples, the stimulation generator of IMD 106 is configured to generate and deliver electrical pulses to patient 112 via electrodes of a selected stimulation electrode combination. However, in other examples, the stimulation generator of IMD 106 may be configured to generate and deliver a continuous wave signal, e.g., a sine wave or triangle wave. In either case, a signal generator within IMD 106 may generate the electrical stimulation therapy for DBS according to a therapy program that is selected at that given time in therapy. In examples in which IMD 106 delivers electrical stimulation in the form of stimulation pulses, a therapy program may include a set of therapy parameter values (e.g., stimulation parameters), such as a stimulation electrode combination for delivering stimulation to patient 112, pulse frequency, pulse width, and a current or voltage amplitude of the pulses. As previously indicated, the electrode combination may indicate the specific electrodes 116, 118 that are selected to deliver stimulation signals to tissue of patient 112 and the respective polarity of the selected electrodes.

IMD 106 may be implanted within a subcutaneous pocket above the clavicle, or, alternatively, the abdomen, back or buttocks of patient 112, on or within cranium 122 or at any other suitable site within patient 112. Generally, IMD 106 is constructed of a biocompatible material that resists corrosion and degradation from bodily fluids. IMD 106 may comprise a hermetic housing to substantially enclose components, such as a processor, therapy module, and memory.

As shown in FIG. 1, implanted lead extension 110 is coupled to IMD 106 via connector 108 (also referred to as a connector block or a header of IMD 106). In the example of FIG. 1, lead extension 110 traverses from the implant site of IMD 106 and along the neck of patient 112 to cranium 122 of patient 112 to access brain 120. In the example shown in FIG. 1, leads 114A and 114B (collectively "leads 114") are implanted within the right and left hemispheres, respectively, of patient 112 in order deliver electrical stimulation to one or more regions of brain 120, which may be selected based on the patient condition or disorder controlled by therapy system 100. The specific target tissue site and the stimulation electrodes used to deliver stimulation to the target tissue site, however, may be selected, e.g., according to the identified patient behaviors and/or other sensed patient parameters. Other lead 114 and IMD 106 implant sites are contemplated. For example, IMD 106 may be implanted on or within cranium 122, in some examples. Or leads 114 may be implanted within the same hemisphere or IMD 106 may be coupled to a single lead.

Existing lead sets include axial leads carrying ring electrodes disposed at different axial positions and so-called "paddle" leads carrying planar arrays of electrodes. Selection of electrode combinations within an axial lead, a paddle lead, or among two or more different leads presents a challenge to the clinician. The emergence of more complex lead array geometries presents still further challenges. The design of the user interface used to program the implantable neurostimulator, in the form of either a clinician programmer or patient programmer, has a great impact on the ability to efficiently define and select efficacious stimulation programs.

Although leads 114 are shown in FIG. 1 as being coupled to a common lead extension 110, in other examples, leads 114 may be coupled to IMD 106 via separate lead extensions or directly to connector 108. Leads 114 may be positioned to deliver electrical stimulation to one or more target tissue sites within brain 120 to manage patient symptoms associated with a movement disorder of patient 112. Leads 114 may be implanted to position electrodes 116, 118 at desired locations of brain 120 through respective holes in cranium 122. Leads 114 may be placed at any location within brain 120 such that electrodes 116, 118 are capable of providing electrical stimulation to target tissue sites within brain 120 during treatment. For example, electrodes 116, 118 may be surgically implanted under the dura mater of brain 120 or within the cerebral cortex of brain 120 via a burr hole in cranium 122 of patient 112, and electrically coupled to IMD 106 via one or more leads 114.

In the example shown in FIG. 1, electrodes 116, 118 of leads 114 are shown as ring electrodes. Ring electrodes may be used in DBS applications because they are relatively simple to program and are capable of delivering an electrical field to any tissue adjacent to electrodes 116, 118. In other examples, electrodes 116, 118 may have different configurations. For example, in some examples, at least some of the electrodes 116, 118 of leads 114 may have a complex electrode array geometry that is capable of producing shaped electrical fields. The complex electrode array geometry may include multiple electrodes (e.g., partial ring or segmented electrodes) around the outer perimeter of each lead 114, rather than one ring electrode. In this manner, electrical stimulation may be directed in a specific direction from leads 114 to enhance therapy efficacy and reduce possible adverse side effects from stimulating a large volume of tissue. In some examples, a housing of IMD 106 may include one or more stimulation and/or sensing electrodes. In alternative examples, leads 114 may have shapes other than elongated cylinders as shown in FIG. 19. For example, leads 114 may be paddle leads, spherical leads, bendable leads, or any other type of shape effective in treating patient 112 and/or minimizing invasiveness of leads 114.

In the example shown in FIG. 1, IMD 106 includes a memory to store a plurality of therapy programs that each define a set of therapy parameter values. In some examples, IMD 106 may select a therapy program from the memory based on various parameters, such as sensed patient parameters and the identified patient behaviors. IMD 106 may generate electrical stimulation based on the selected therapy program to manage the patient symptoms associated with a movement disorder.

External programmer 104 wirelessly communicates with IMD 106 as needed to provide or retrieve therapy information. Programmer 104 is an external computing device that the user, e.g., a clinician and/or patient 112, may use to communicate with IMD 106. For example, programmer 104 may be a clinician programmer that the clinician uses to communicate with IMD 106 and program one or more therapy programs for IMD 106. Alternatively, programmer 104 may be a patient programmer that allows patient 112 to select programs and/or view and modify therapy parameters. The clinician programmer may include more programming features than the patient programmer. In other words, more complex or sensitive tasks may only be allowed by the clinician programmer to prevent an untrained patient from making undesirable changes to IMD 106. In other examples, programmer 104 may be configured to receive user annotations for adjusting the location of atlas-defined anatomical structures with respect to a representation of patient-specific anatomy.

When programmer 104 is configured for use by the clinician, programmer 104 may be used to transmit initial programming information to IMD 106. This initial information may include hardware information, such as the type of leads 114 and the electrode arrangement, the position of leads 114 within brain 120, the configuration of electrode array 116, 118, initial programs defining therapy parameter values, and any other information the clinician desires to program into IMD 106. Programmer 104 may also be capable of completing functional tests (e.g., measuring the impedance of electrodes 116, 118 of leads 114).

The clinician may also store therapy programs within IMD 106 with the aid of programmer 104. During a programming session, the clinician may determine one or more therapy programs that may provide efficacious therapy to patient 112 to address symptoms associated with the patient condition, and, in some cases, specific to one or more different patient states, such as a sleep state, movement state or rest state. For example, the clinician may select one or more stimulation electrode combination with which stimulation is delivered to brain 120. During the programming session, patient 112 may provide feedback to the clinician as to the efficacy of the specific program being evaluated or the clinician may evaluate the efficacy based on one or more physiological parameters of patient 112 (e.g., muscle activity or muscle tone). Alternatively, identified patient behavior from video information may be used as feedback during the initial, and subsequent programming sessions. Programmer 104 may assist the clinician in the creation/identification of therapy programs by providing a methodical system for identifying potentially beneficial therapy parameter values.

Programmer 104 may also be configured for use by patient 112. When configured as a patient programmer, programmer 104 may have limited functionality (compared to a clinician programmer) in order to prevent patient 112 from altering critical functions of IMD 106 or applications that may be detrimental to patient 112. In this manner, programmer 104 may only allow patient 112 to adjust values for certain therapy parameters or set an available range of values for a particular therapy parameter.

Programmer 104 may also provide an indication to patient 112 when therapy is being delivered, when patient input has triggered a change in therapy or when the power source within programmer 104 or IMD 106 needs to be replaced or recharged. For example, programmer 112 may include an alert LED, may flash a message to patient 112 via a programmer display, generate an audible sound or somatosensory cue to confirm patient input was received, e.g., to indicate a patient state or to manually modify a therapy parameter.

Therapy system 100 may be implemented to provide chronic stimulation therapy to patient 112 over the course of several months or years. However, system 100 may also be employed on a trial basis to evaluate therapy before committing to full implantation. If implemented temporarily, some components of system 100 may not be implanted within patient 112. For example, patient 112 may be fitted with an external medical device, such as a trial stimulator, rather than IMD 106. The external medical device may be coupled to percutaneous leads or to implanted leads via a percutaneous extension. If the trial stimulator indicates DBS system 100 provides effective treatment to patient 112, the clinician may implant a chronic stimulator within patient 112 for relatively long-term treatment.

Although IMD 104 is described as delivering electrical stimulation therapy to brain 120, IMD 106 may be configured to direct electrical stimulation to other anatomical regions of patient 112. In other examples, system 100 may include an implantable drug pump in addition to, or in place of, IMD 106. Further, an IMD may provide other electrical stimulation such as spinal cord stimulation to treat a movement disorder.

The techniques described herein may be used during a test or evaluation mode to select different electrode combinations in an effort to identify efficacious electrode combinations. Additionally, the techniques may be used to select different electrode combinations associated with different stimulation programs during an operational mode, either directly or by selection of programs including such electrode combinations. For example, the techniques and associated user interfaces may be implemented in a clinician programmer used by a clinician to program a stimulator, in a patient programmer used by a patient to program or control a stimulator, or in an external stimulator including both pulse generation and programming functionality.

System 100 may receive one or more images of patient anatomy and present at least a portion of an anatomical atlas in conjunction with (e.g., overlaid or along with) the representation of the patient anatomy for display to the clinician. The images of patient anatomy may have been generated using one or more imaging modalities, such as magnetic resonance imaging (MRI), x-ray, computerized tomography (CT), positron emission tomography (PET), or any other imaging modality capable of visualizing the desired anatomy of the patient. System 100, such as programmer 104 or a networked server (not shown in FIG. 1) may automatically overlay one or more reference atlases over the patient image to indicate the location of certain structures within the patient anatomy. However, since the structures of the atlas may differ in size, shape, and/or location to the corresponding structures of the patient anatomy, system 100 may not correctly align the structures of the anatomical atlas with the structures of the patient anatomy illustrated in the representation.

To more accurately align the atlas with the patient anatomy, system 100 may be configured to receive, via a user interface, a user annotation that indicates a location with respect to the patient anatomy at which the atlas structure should be located. For example, programmer 104 may present a user interface that displays one or more structures of the atlas in conjunction with a representation of the patient anatomy. Programmer 104 may also provide one or more annotation tools provided by the user interface that allow a clinician to provide the user annotation input. For example, in one or more views of the patient image, the clinician may provide the annotation that is received by programmer 104. The user annotation received by programmer 104 may that indicate where one or more structures of the atlas should be located with respect to the image representing the patient anatomy. Based on the user annotation, the system 100 may adjust the position of one or more structures of the anatomical atlas to more closely align with the patient anatomy. System 100 may then use the adjusted anatomical atlas to indicate structures of patient anatomy that can be used when determining stimulation parameters that define subsequent electrical stimulation therapy. Based on the adjusted anatomical atlas and/or user input, system 100 may be configured to select a target anatomical region of patient 112. IMD 106 may then be configured to generate a set of stimulation parameters and deliver stimulation therapy to the target anatomical region of patient 112 via electrodes 116, 118 of lead 114 based on the generated set of stimulation parameters.

Accordingly, the techniques of the disclosure may allow a system to more accurately correlate representative structures defined by an anatomical atlas to anatomical structures of the patient based on user annotation. In doing so, the clinician may use the adjusted atlas to more accurately select stimulation parameters directed to the targeted anatomical structures of the patient. Such targeted therapy may allow a clinician to deliver more precise control over which areas of the brain receive therapy. Further, the techniques may allow the clinician to partially or completely disregard the electrode locations and focus on selecting the structures that need to be stimulated to treat the patient may decrease clinician time and confusion in configuring the electrical stimulation, and increase therapy efficacy.

The architecture of system 100 illustrated in FIG. 1 is shown as an example. The techniques as set forth in this disclosure may be implemented in the example system 100 of FIG. 1, as well as other types of systems not described specifically herein. Nothing in this disclosure should be construed so as to limit the techniques of this disclosure to the example architecture illustrated by FIG. 1.

Figure 2:
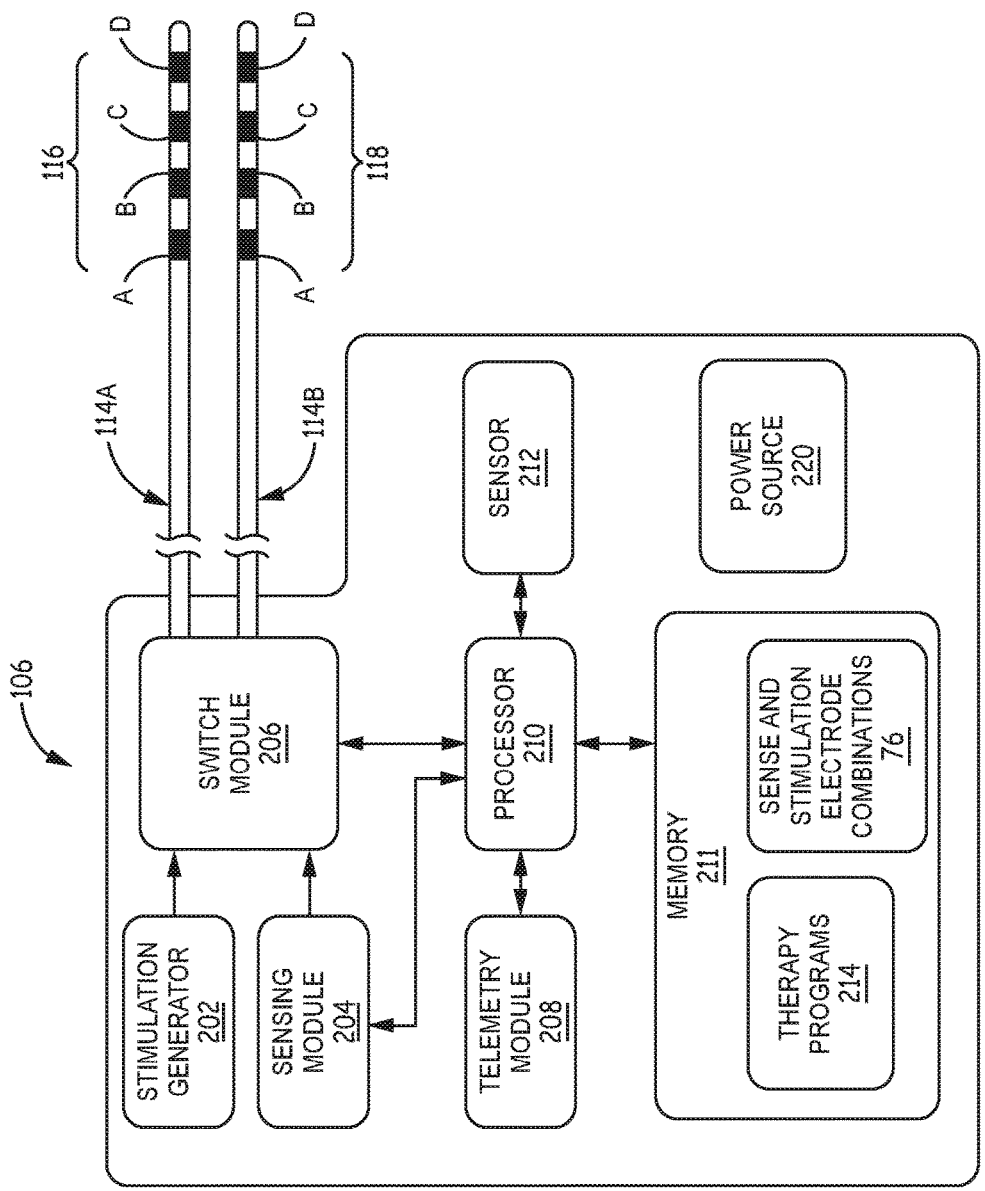
FIG. 2 is a block diagram of the example IMD of FIG. 1 for delivering deep brain stimulation therapy.

FIG. 2 is a block diagram of the example IMD 106 of FIG. 1 for delivering deep brain stimulation therapy. In the example shown in FIG. 2, IMD 106 includes processor 210, memory 211, stimulation generator 202, sensing module 204, switch module 206, telemetry module 208, sensor 212, and power source 220. Each of these modules may be or include electrical circuitry configured to perform the functions attributed to each respective module. For example, processor 210 may include processing circuitry, switch module 206 may include switch circuitry, sensing module 204 may include sensing circuitry, and telemetry module 208 may include telemetry circuitry. Memory 211 may include any volatile or non-volatile media, such as a random access memory (RAM), read only memory (ROM), non-volatile RAM (NVRAM), electrically erasable programmable ROM (EEPROM), flash memory, and the like. Memory 211 may store computer-readable instructions that, when executed by processor 210, cause IMD 106 to perform various functions. Memory 211 may be a storage device or other non-transitory medium.

In the example shown in FIG. 2, memory 211 stores therapy programs 214 and sense electrode combinations and associated stimulation electrode combinations 218 in separate memories within memory 211 or separate areas within memory 211. Each stored therapy program 214 defines a particular set of electrical stimulation parameters (e.g., a therapy parameter set), such as a stimulation electrode combination, electrode polarity, current or voltage amplitude, pulse width, and pulse rate. In some examples, individual therapy programs may be stored as a therapy group, which defines a set of therapy programs with which stimulation may be generated. The stimulation signals defined by the therapy programs of the therapy group may be delivered together on an overlapping or non-overlapping (e.g., time-interleaved) basis.

Sense and stimulation electrode combinations 218 stores sense electrode combinations and associated stimulation electrode combinations. As described above, in some examples, the sense and stimulation electrode combinations may include the same subset of electrodes 116, 118, or may include different subsets of electrodes. Thus, memory 211 can store a plurality of sense electrode combinations and, for each sense electrode combination, store information identifying the stimulation electrode combination that is associated with the respective sense electrode combination. The associations between sense and stimulation electrode combinations can be determined, e.g., by a clinician or automatically by processor 210. In some examples, corresponding sense and stimulation electrode combinations may comprise some or all of the same electrodes. In other examples, however, some or all of the electrodes in corresponding sense and stimulation electrode combinations may be different. For example, a stimulation electrode combination may include more electrodes than the corresponding sense electrode combination in order to increase the efficacy of the stimulation therapy. In some examples, as discussed above, stimulation may be delivered via a stimulation electrode combination to a tissue site that is different than the tissue site closest to the corresponding sense electrode combination but is within the same region, e.g., the thalamus, of brain 120 in order to mitigate any irregular oscillations or other irregular brain activity within the tissue site associated with the sense electrode combination.

Stimulation generator 202, under the control of processor 210, generates stimulation signals for delivery to patient 112 via selected combinations of electrodes 116, 118. An example range of electrical stimulation parameters believed to be effective in DBS to manage a movement disorder of patient include:

1. Frequency: between approximately 100 Hz and approximately 500 Hz, such as approximately 130 Hz.

2. Voltage Amplitude: between approximately 0.1 volts and approximately 50 volts, such as between approximately 0.5 volts and approximately 20 volts, or approximately 5 volts.

3. Current Amplitude: A current amplitude may be defined as the biological load in which the voltage is delivered. In a current-controlled system, the current amplitude, assuming a lower level impedance of approximately 500 ohms, may be between approximately 0.2 milliamps to approximately 100 milliamps, such as between approximately 1 milliamps and approximately 40 milliamps, or approximately 10 milliamps. However, in some examples, the impedance may range between about 200 ohms and about 2 kiloohms.

4. Pulse Width: between approximately 10 microseconds and approximately 5000 microseconds, such as between approximately 100 microseconds and approximately 1000 microseconds, or between approximately 180 microseconds and approximately 450 microseconds.

Accordingly, in some examples, stimulation generator 202 generates electrical stimulation signals in accordance with the electrical stimulation parameters noted above. Other ranges of therapy parameter values may also be useful, and may depend on the target stimulation site within patient 112. While stimulation pulses are described, stimulation signals may be of any form, such as continuous-time signals (e.g., sine waves) or the like.

Processor 210 may include any one or more of a microprocessor, a controller, a digital signal processor (DSP), an application specific integrated circuit (ASIC), a field-programmable gate array (FPGA), discrete logic circuitry, or any other processing circuitry configured to provide the functions attributed to processor 210 herein may be embodied as firmware, hardware, software or any combination thereof. Processor 210 controls stimulation generator 202 according to therapy programs 214 stored in memory 211 to apply particular stimulation parameter values specified by one or more of programs, such as amplitude, pulse width, and pulse rate.

In the example shown in FIG. 2, the set of electrodes 116 includes electrodes 116A, 116B, 116C, and 116D, and the set of electrodes 118 includes electrodes 118A, 118B, 118C, and 118D. Processor 210 also controls switch module 206 to apply the stimulation signals generated by stimulation generator 202 to selected combinations of electrodes 116, 118. In particular, switch module 204 may couple stimulation signals to selected conductors within leads 114, which, in turn, deliver the stimulation signals across selected electrodes 116, 118. Switch module 206 may be a switch array, switch matrix, multiplexer, or any other type of switching module configured to selectively couple stimulation energy to selected electrodes 116, 118 and to selectively sense bioelectrical brain signals with selected electrodes 116, 118. Hence, stimulation generator 202 is coupled to electrodes 116, 118 via switch module 206 and conductors within leads 114. In some examples, however, IMD 106 does not include switch module 206.

Stimulation generator 202 may be a single channel or multi-channel stimulation generator. In particular, stimulation generator 202 may be capable of delivering a single stimulation pulse, multiple stimulation pulses, or a continuous signal at a given time via a single electrode combination or multiple stimulation pulses at a given time via multiple electrode combinations. In some examples, however, stimulation generator 202 and switch module 206 may be configured to deliver multiple channels on a time-interleaved basis. For example, switch module 206 may serve to time divide the output of stimulation generator 202 across different electrode combinations at different times to deliver multiple programs or channels of stimulation energy to patient 112.

Electrodes 116, 118 on respective leads 114 may be constructed of a variety of different designs. For example, one or both of leads 114 may include two or more electrodes at each longitudinal location along the length of the lead, such as multiple electrodes at different perimeter locations around the perimeter of the lead at each of the locations A, B, C, and D. On one example, the electrodes may be electrically coupled to switch module 206 via respective wires that are straight or coiled within the housing the lead and run to a connector at the proximal end of the lead. In another example, each of the electrodes of the lead may be electrodes deposited on a thin film. The thin film may include an electrically conductive trace for each electrode that runs the length of the thin film to a proximal end connector. The thin film may then be wrapped (e.g., a helical wrap) around an internal member to form the lead 114. These and other constructions may be used to create a lead with a complex electrode geometry.

Although sensing module 204 is incorporated into a common housing with stimulation generator 202 and processor 210 in FIG. 2, in other examples, sensing module 204 may be in a separate housing from IMD 106 and may communicate with processor 210 via wired or wireless communication techniques. Example bioelectrical brain signals include, but are not limited to, a signal generated from local field potentials within one or more regions of brain 28. EEG and ECoG signals are examples of local field potentials that may be measured within brain 120. However, local field potentials may include a broader genus of electrical signals within brain 120 of patient 112.

Sensor 212 may include one or more sensing elements that sense values of a respective patient parameter. For example, sensor 212 may include one or more accelerometers, optical sensors, chemical sensors, temperature sensors, pressure sensors, or any other types of sensors. Sensor 212 may output patient parameter values that may be used as feedback to control delivery of therapy. IMD 106 may include additional sensors within the housing of IMD 106 and/or coupled via one of leads 114 or other leads. In addition, IMD 106 may receive sensor signals wirelessly from remote sensors via telemetry module 208, for example. In some examples, one or more of these remote sensors may be external to patient (e.g., carried on the external surface of the skin, attached to clothing, or otherwise positioned external to the patient).

Telemetry module 208 supports wireless communication between IMD 106 and an external programmer 104 or another computing device under the control of processor 210. Processor 210 of IMD 106 may receive, as updates to programs, values for various stimulation parameters such as amplitude and electrode combination, from programmer 104 via telemetry module 208. The updates to the therapy programs may be stored within therapy programs 214 portion of memory 211. Telemetry module 208 in IMD 106, as well as telemetry modules in other devices and systems described herein, such as programmer 104, may accomplish communication by radiofrequency (RF) communication techniques. In addition, telemetry module 208 may communicate with external medical device programmer 104 via proximal inductive interaction of IMD 106 with programmer 104. Accordingly, telemetry module 208 may send information to external programmer 104 on a continuous basis, at periodic intervals, or upon request from IMD 106 or programmer 104.

Power source 220 delivers operating power to various components of IMD 106. Power source 220 may include a small rechargeable or non-rechargeable battery and a power generation circuit to produce the operating power. Recharging may be accomplished through proximal inductive interaction between an external charger and an inductive charging coil within IMD 220. In some examples, power requirements may be small enough to allow IMD 220 to utilize patient motion and implement a kinetic energy-scavenging device to trickle charge a rechargeable battery. In other examples, traditional batteries may be used for a limited period of time.

System 100 may receive one or more images of patient anatomy and present at least a portion of an anatomical atlas over the representation of the patient anatomy for display to the clinician. Since system 100 may not automatically align the structures of the anatomical atlas correctly with the structures of the patient anatomy illustrated in the representation, system 100 may receive, via a user interface, a user annotation that indicates a location with respect to the patient anatomy at which the atlas structure should be located. For example, the clinician may provide input one in one or more views of the patient image that indicates where a structure of the atlas should be located with respect to the patient image. Based on the user annotation, the system 100 may adjust the position of one or more structures of the anatomical atlas to more closely align with the patient anatomy. System 100 may then use the adjusted anatomical atlas to indicate structures of patient anatomy that can be used when determining stimulation parameters that define subsequent electrical stimulation therapy. Based on the adjusted anatomical atlas, system 100 selects a target anatomical region of patient 112. IMD 106 delivers therapy to the target anatomical region of patient 112 via electrodes 116, 118 of lead 114.

Accordingly, the techniques of the disclosure may allow for a clinician to more accurately map representative structures defined by an anatomical atlas to anatomical structures of the patient. In doing so, the clinician may more accurately deliver therapy to the targeted anatomical structures of the patient. Such targeted therapy may allow a clinician to deliver more precise control over which areas of the brain receive therapy. Further, the techniques may allow the clinician to partially or completely disregard the electrode locations and focus on selecting the structures that need to be stimulated to treat the patient may decrease clinician time and confusion in configuring the electrical stimulation, and increase therapy efficacy.

The architecture of IMD 106 illustrated in FIG. 2 is shown as an example. The techniques as set forth in this disclosure may be implemented in the example IMD 106 of FIG. 2, as well as other types of systems not described specifically herein. Nothing in this disclosure should be construed so as to limit the techniques of this disclosure to the example architecture illustrated by FIG. 2.

Figure 3:
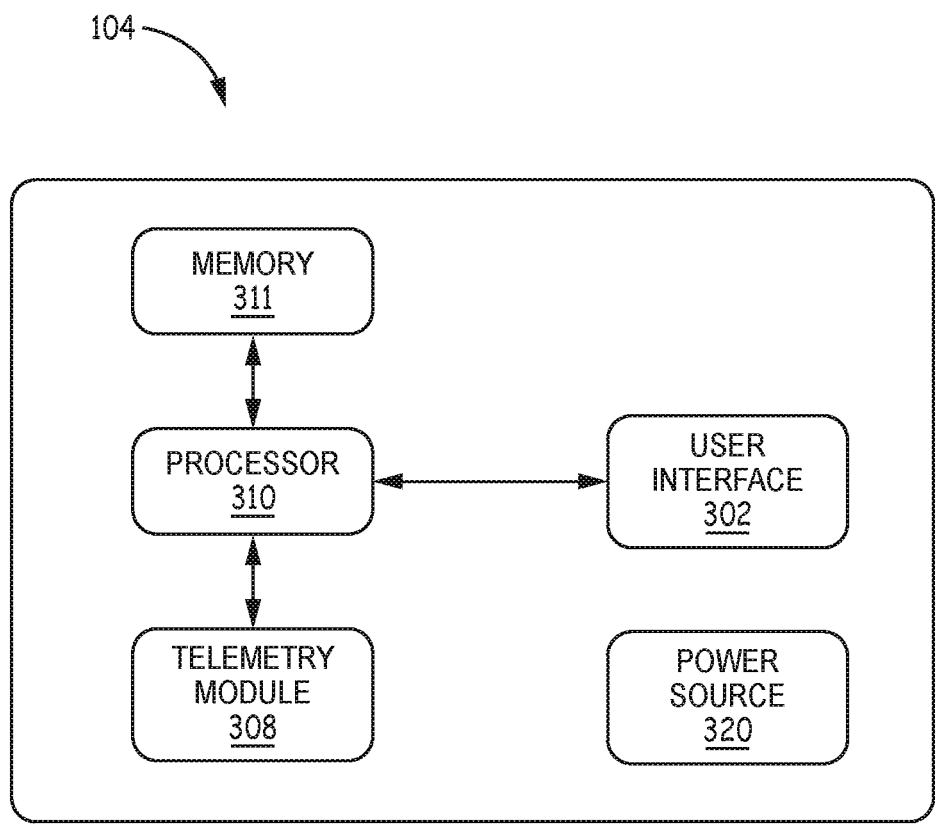
FIG. 3 is a block diagram of the external programmer of FIG. 1.

FIG. 3 is a block diagram of the external programmer 104 of FIG. 1. Although programmer 104 may generally be described as a hand-held device, programmer 104 may be a larger portable device or a more stationary device. In addition, in other examples, programmer 104 may be included as part of an external charging device or include the functionality of an external charging device. As illustrated in FIG. 3, programmer 104 may include a processor 310, memory 311, user interface 302, telemetry module 308, and power source 320. Memory 311 may store instructions that, when executed by processor 310, cause processor 310 and external programmer 104 to provide the functionality ascribed to external programmer 104 throughout this disclosure. Each of these components, or modules, may include electrical circuitry that is configured to perform some or all of the functionality described herein. For example, processor 310 may include processing circuitry configured to perform the processes discussed with respect to processor 310.

In general, programmer 104 comprises any suitable arrangement of hardware, alone or in combination with software and/or firmware, to perform the techniques attributed to programmer 104, and processor 310, user interface 302, and telemetry module 308 of programmer 104. In various examples, programmer 104 may include one or more processors, such as one or more microprocessors, DSPs, ASICs, FPGAs, or any other equivalent integrated or discrete logic circuitry, as well as any combinations of such components. Programmer 104 also, in various examples, may include a memory 311, such as RAM, ROM, PROM, EPROM, EEPROM, flash memory, a hard disk, a CD-ROM, comprising executable instructions for causing the one or more processors to perform the actions attributed to them. Moreover, although processor 310 and telemetry module 308 are described as separate modules, in some examples, processor 310 and telemetry module 308 are functionally integrated. In some examples, processor 310 and telemetry module 308 correspond to individual hardware units, such as ASICs, DSPs, FPGAs, or other hardware units.

Memory 311 (e.g., a storage device) may store instructions that, when executed by processor 310, cause processor 310 and programmer 104 to provide the functionality ascribed to programmer 104 throughout this disclosure. For example, memory 311 may include instructions that cause processor 310 to obtain a parameter set from memory, select a spatial electrode movement pattern, or receive a user input and send a corresponding command to IMD 104, or instructions for any other functionality. In addition, memory 311 may include a plurality of programs, where each program includes a parameter set that defines stimulation therapy.

User interface 302 may include a button or keypad, lights, a speaker for voice commands, a display, such as a liquid crystal (LCD), light-emitting diode (LED), or organic light-emitting diode (OLED). In some examples, the display may be a touch screen. User interface 302 may be configured to display any information related to the delivery of stimulation therapy, identified patient behaviors, sensed patient parameter values, patient behavior criteria, or any other such information. User interface 302 may also receive user input via user interface 302. The input may be, for example, in the form of pressing a button on a keypad or selecting an icon from a touch screen. The input may request starting or stopping electrical stimulation, the input may request a new spatial electrode movement pattern or a change to an existing spatial electrode movement pattern, of the input may request some other change to the delivery of electrical stimulation.

Processor 310 may also control user interface 302 to display information related to an anatomical atlas (e.g., an atlas of a reference anatomy) and patient-specific anatomy. For example, user interface 302 may display a representation of one or more atlas-defined anatomical structures over a representation (e.g., an image) of the specific patient anatomy. User interface 302 may present annotation tools for adjusting the structures of the atlas to the patient anatomy and receive user annotations indicating where the corresponding structures of the patient anatomy are located and/or where the atlas should be moved with respect to the patient anatomy. Processor 310 may then adjust the position and/or size of the structures of the atlas to more closely match (e.g., a best fit) to the user annotation. After the atlas has been adjusted, the user may refer to the atlas for locations of certain structures of the patient instead of needing to continually find desired structures based on the image of the patient anatomy.

Telemetry module 308 may support wireless communication between IMD 106 and programmer 104 under the control of processor 310. Telemetry module 308 may also be configured to communicate with another computing device via wireless communication techniques, or direct communication through a wired connection. In some examples, telemetry module 308 provides wireless communication via an RF or proximal inductive medium. In some examples, telemetry module 308 includes an antenna, which may take on a variety of forms, such as an internal or external antenna.

Examples of local wireless communication techniques that may be employed to facilitate communication between programmer 104 and IMD 106 include RF communication according to the 802.11 or Bluetooth specification sets or other standard or proprietary telemetry protocols. In this manner, other external devices may be capable of communicating with programmer 104 without needing to establish a secure wireless connection. As described herein, telemetry module 308 may be configured to transmit a spatial electrode movement pattern or other stimulation parameter values to IMD 106 for delivery of stimulation therapy.

In some examples, selection of therapy parameters or therapy programs may be transmitted to a medical device (e.g., IMD 106) for delivery to patient 112. In other examples, the therapy may include medication, activities, or other instructions that patient 112 must perform themselves or a caregiver perform for patient 112. In some examples, programmer 104 may provide visual, audible, and/or tactile notifications that indicate there are new instructions. Programmer 104 may require receiving user input acknowledging that the instructions have been completed in some examples.

The architecture of programmer 104 illustrated in FIG. 3 is shown as an example. The techniques as set forth in this disclosure may be implemented in the example programmer 104 of FIG. 3, as well as other types of systems not described specifically herein. Nothing in this disclosure should be construed so as to limit the techniques of this disclosure to the example architecture illustrated by FIG. 3.

Figure 4:
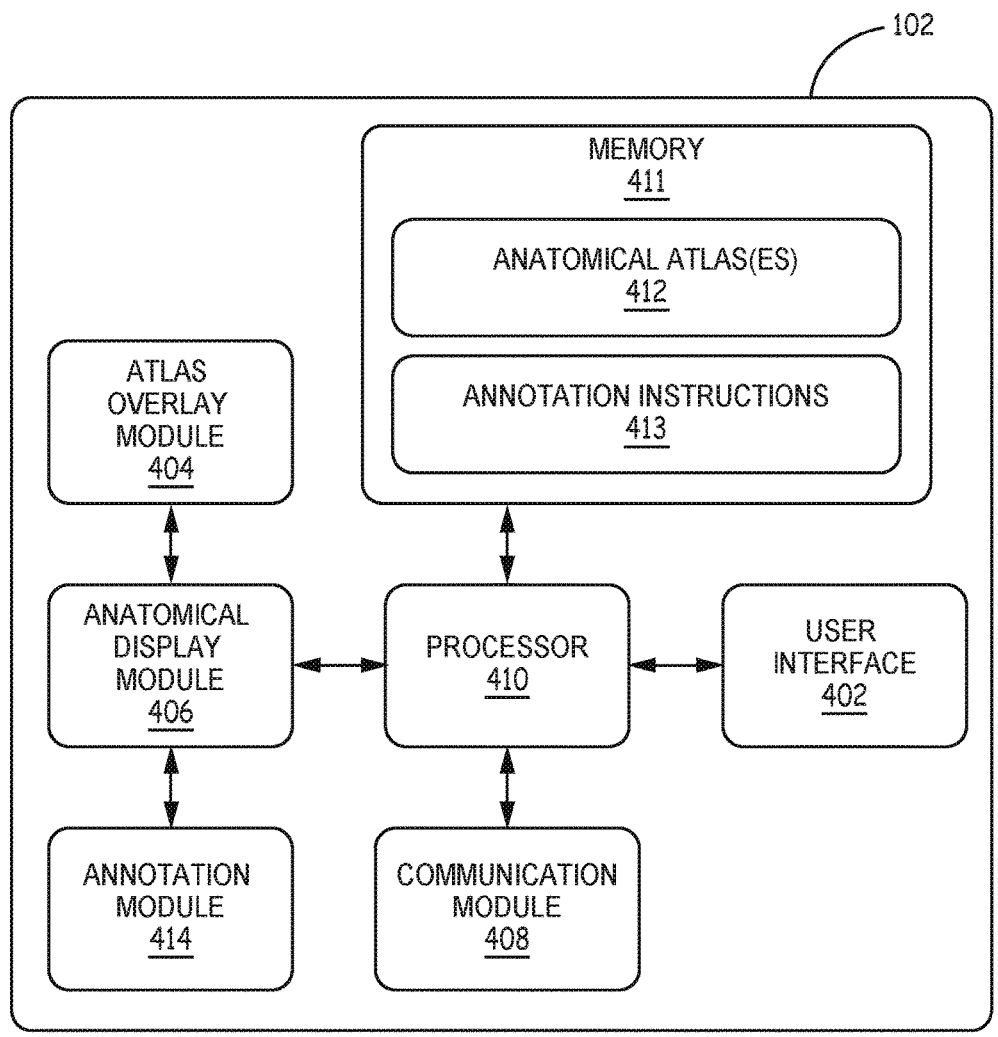
FIG. 4 is a block diagram of a networked server configured to place anatomical atlases with respect to representations of anatomical regions of a patient according to the techniques of the disclosure.

FIG. 4 is a block diagram of a networked server 102 (also shown in FIG. 5) configured to place anatomical atlases with respect to representations of anatomical regions of a patient 112 according to the techniques of the disclosure. As illustrated in FIG. 4, server 102 may include a processor 410, a memory 411, a user interface 402, a communication module 408, an atlas overlay module 404, anatomical display module 406, and an annotation module 414.

In various examples, server 102 may include one or more processors 410, such as one or more microprocessors, DSPs, ASICs, FPGAs, or any other equivalent integrated or discrete logic circuitry, as well as any combinations of such components. Server 102 also, in various examples, may include a memory 411, such as RAM, ROM, PROM, EPROM, EEPROM, flash memory, a hard disk, a CD-ROM, comprising executable instructions for causing the one or more processors to perform the actions attributed to them. Moreover, although processor 410 and communications module 408 are described as separate modules, in some examples, processor 408 and communications module 408 are functionally integrated. In some examples, processor 410 and communications module 408 correspond to individual hardware units, such as ASICs, DSPs, FPGAs, or other hardware units. The modules of network server 102 may be or include processing circuitry or other electrical circuitry configured to provide the functionality described herein. For example, processor 410 may include processing circuitry configured to perform the processes discussed with respect to processor 410.

Memory 411 (e.g., a storage device) may store instructions that, when executed by processor 410, cause processor 410 and network server 102 to provide the functionality ascribed to network server 102 throughout this disclosure. For example, memory 411 may include instructions that cause processor 410 to receive one or more images of patient anatomy and present at least a portion of an anatomical atlas over the representation of the patient anatomy. Memory 411 may further include instructions that cause processor 410 to receive, via a user interface 402, a user annotation that indicates a location with respect to the patient anatomy at which the atlas structure should be located and adjust the position of one or more structures of the anatomical atlas to more closely align with the patient anatomy. Further, memory 411 may include instructions that cause processor 410 to cause IMD 106 to deliver therapy to patient 112 according to the adjusted one or more structures of the anatomical atlas.

In some examples, memory 411 stores one or more anatomical atlases 412. In this example, anatomical atlases 412 define one or more structures of the brain. These structures may comprise representative structures created by aggregated information over a group of patients. some examples, memory 411 further stores one or more annotation instructions 413. Annotation instructions 413 provide instructions to processor 410 for adjusting a position of a structure defined by one or more anatomical atlases 412 with respect to an anatomical representation of patient 112. Anatomical atlases 412 and/or annotation instructions 413 may be stored within memory 411 of networked server 102 or at one or more repositories external to networked server 102. In addition, memory 411 or another repository may store images of patient anatomy that are accessible by processor 410 and/or other modules of networked server 102.

Communications module 408 supports wired or wireless communication between server 102 and another computing device, such as IMD 106, external programmer 104, or another computing device under the control of processor 410. Processor 210 of IMD 106 may receive, as updates to programs, values for various stimulation parameters such as amplitude and electrode combination, from programmer 104 via telemetry module 208. The updates to the therapy programs may be stored within therapy programs 214 portion of memory 211. Telemetry module 208 in IMD 106, as well as telemetry modules in other devices and systems described herein, such as programmer 104, may accomplish communication by radiofrequency (RF) communication techniques. In addition, telemetry module 208 may communicate with external medical device programmer 104 via proximal inductive interaction of IMD 106 with programmer 104. Accordingly, telemetry module 208 may send information to external programmer 104 on a continuous basis, at periodic intervals, or upon request from IMD 106 or programmer 104.

In some examples, server 102 includes an anatomical display module 406. Anatomical display module 406 is configured to generate, for display via user interface 402, a representation of one or more anatomical structures of patient 112. These representations may be generated by one or more images or data obtained from an imaging modality that was used to image the patient. In some examples, anatomical display module 406 is configured to provide the representation of the one or more anatomical structures in more than one view. For example, anatomical display module 406 may provide orthogonal and/or oblique 2D views of the one or more anatomical structures (e.g., along a coronal, sagittal, and axial plane). Further, anatomical display module 406 may provide views of the one or more anatomical structures in a three-dimensional view. In some examples, server 102 may include the user interface 402. In other examples, processor 410 and/or user interface 402 may control a user interface of a different device (e.g., programmer 104) to display information and/or receive user input.

Server 102 further includes an atlas overlay module 404. Atlas overlay module 404 retrieves one or more structures of anatomical atlases 412 stored in memory 411 and overlays the structures over the representation of the one or more anatomical structures of patient 112. Anatomical display module 406 is configured to provide, for display via user interface 402, a representation of one or more anatomical structures of patient 112 having the overlaid representative structures. In other examples, atlas overlay module 404 may provide atlas information that is to be displayed in conjunction with the representation of patient anatomy but not overlaid. For example, the representation of the atlas may be provided instead of a portion of the patient anatomy representation or the representation of the patient anatomy may be laid over the atlas.

Server 102 further includes an annotation module 414. Annotation module 414 may overlay an annotation over the representation of the one or more anatomical structures of patient 112. In some examples, the annotation may represent the approximate location, shape, and/or size of one or more of the structures overlaid on the representation of the patient. Annotation module 414 may, via user interface 402, receive adjustments to the annotation from a clinician. For example, the annotation may include one or more "control points." The clinician may, via user interface 402, click and drag the control points on the annotation to change the shape of the annotation. Put another way, user interface 402 may generate and provide one or more control points, receive user input manipulating the control points, and adjust the annotation based on the user input manipulating each control point. User interface 402 may receive other types of annotations such as user-drawn outlines or pre-determined shape templates as representative of the patient anatomical structures. In this fashion, the clinician may manipulate the shape of the annotation to approximate the shape of an anatomical structure of the patient. In response to this annotation, atlas overlay module 404 may adjust the position of the representative structures defined by atlases 412 with respect to the representation of the one or more anatomical structures of patient 112. Based on the location of the adjusted position of the structures defined by the atlas, processor 410, via communication module 408, instructs IMD 102 to deliver electrical stimulation to patient 112.

Accordingly, the techniques of the disclosure may allow for a clinician to more accurately map representative structures defined by an anatomical atlas to anatomical structures of the patient. In doing so, the clinician may more accurately deliver therapy to the targeted anatomical structures of the patient. Such targeted therapy may allow a clinician to deliver more precise control over which areas of the brain receive therapy. Further, the techniques may allow the clinician to partially or completely disregard the electrode locations and focus on selecting the structures that need to be stimulated to treat the patient may decrease clinician time and confusion in configuring the electrical stimulation, and increase therapy efficacy.

The architecture of network server 102 illustrated in FIG. 4 is shown as an example. The techniques as set forth in this disclosure may be implemented in the example server 102 of FIG. 4, as well as other types of systems not described specifically herein. Nothing in this disclosure should be construed so as to limit the techniques of this disclosure to the example architecture illustrated by FIG. 4.

Figure 5:
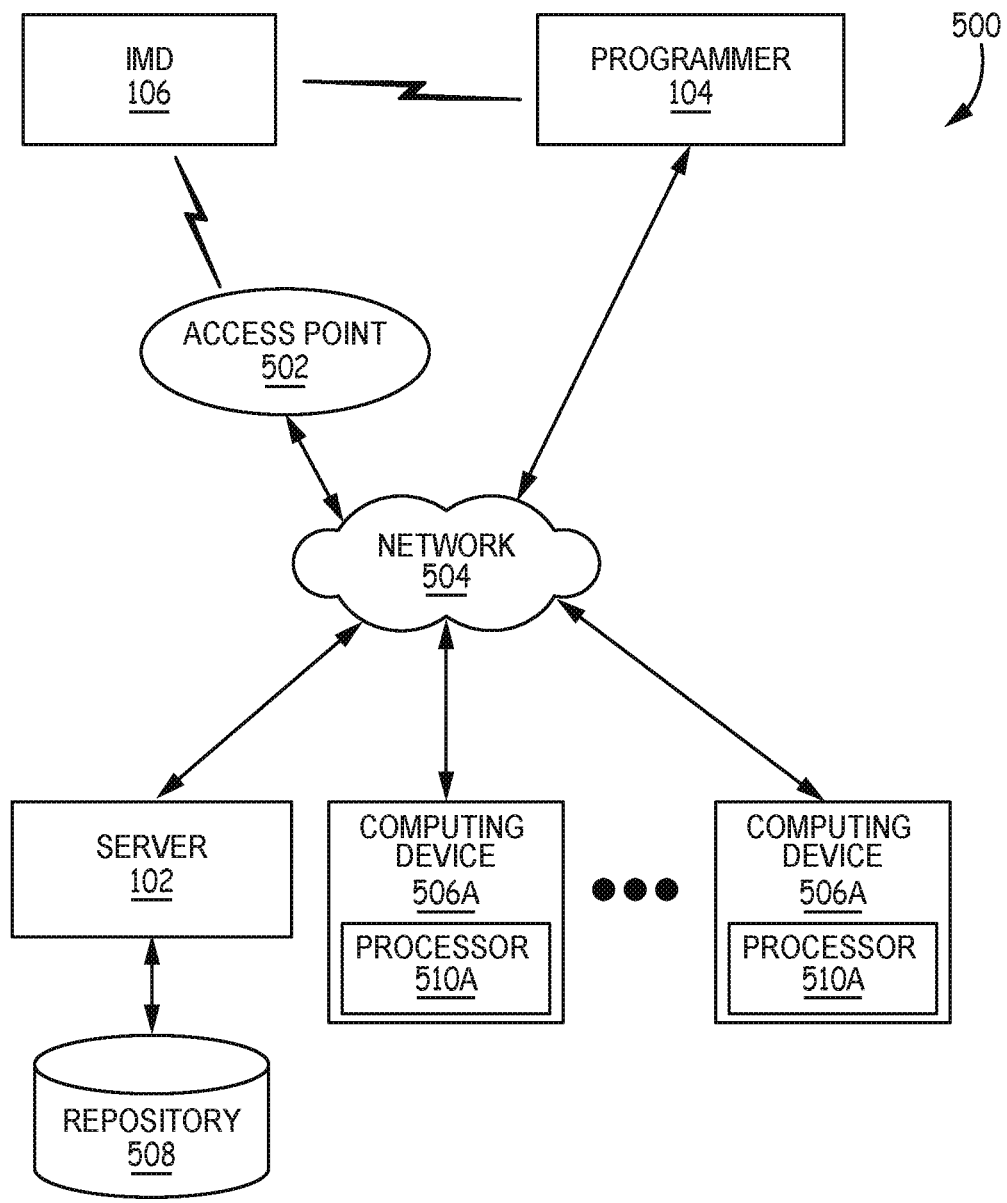
FIG. 5 is a block diagram illustrating an example system that includes the networked server of FIG. 1, the IMD of FIG. 1, and one or more computing devices in communication via a network.

FIG. 5 is a block diagram illustrating an example system that includes the networked server of FIG. 4, the IMD of FIG. 1, and one or more computing devices in communication via a network. System 500 may be similar to system 100 of FIG. 1. As shown in FIG. 5, server 102 (e.g., a networked external computing device) and one or more computing devices 506A-506N that are coupled to the IMD 106 and programmer 104 of FIG. 1 via a network 504. Network 504 may be generally used to transmit information, such as patient imaging data, atlases, user annotations, therapy parameter information, or any other data between IMD 106, programmer 104, server 102 and/or computing devices 506.

In some examples, the information transmitted by IMD 106 may allow a clinician or other healthcare professional to monitor patient 112 remotely. In some examples, IMD 106 may use a telemetry module to communicate with programmer 106 via a first wireless connection, and to communicate with access point 502 via a second wireless connection, e.g., at different times. In the example of FIG. 5, access point 502, programmer 104, server 102, and computing devices 506A-506N are interconnected, and able to communicate with each other through network 504. In some cases, one or more of access point 502, programmer 104, server 102 and computing devices 506A-506N may be coupled to network 102 via one or more wireless connections. IMD 106, programmer 104, server 102, and computing devices 506A-506N may each comprise one or more processors, such as one or more microprocessors, DSPs, ASICs, FPGAs, programmable logic circuitry, or the like, that may perform various functions and operations, such as those described herein.

Access point 502 may comprise a device that connects to network 504 via any of a variety of connections, such as telephone dial-up, digital subscriber line (DSL), or cable modem connections. In other examples, access point 502 may be coupled to network 504 through different forms 502 connections, including wired or wireless connections. In some examples, access point 502 may be co-located with patient 112 and may comprise one or more programming units and/or computing devices (e.g., one or more monitoring units) that may perform various functions and operations described herein. For example, access point 502 may include a home-monitoring unit that is co-located with patient 112 and that may monitor the activity of IMD 106. In some examples, server 102 or computing devices 506 may control or perform any of the various functions or operations described herein.

In some cases, server 102 may be configured to provide a secure storage site for archival of video information, therapy parameters, patient parameters, or other data that has been collected and generated from IMD 106 and/or programmer 104. Network 504 may comprise a local area network, wide area network, or global network, such as the Internet. The system of FIG. 5 may be implemented, in some aspects, with general network technology and functionality similar to that provide by the Medtronic CareLink® Network developed by Medtronic, Inc., of Minneapolis, Minn.

According to the techniques of the disclosure, server 102 may control a user interface to display a representation of one or more anatomical structures of patient 112. Server 102 further provides one or more structures of an anatomical atlas overlaid over the representation of the one or more anatomical structures of patient 112. Server 102 further displays an annotation over the representation of the one or more anatomical structures of patient 112. In some examples, the annotation may closely approximate one or more of the structures overlaid on the representation of the patient. Server 102 may, via user interface 402, receive adjustments to the annotation from a clinician. In this fashion, the clinician may manipulate the shape of the annotation to adjust or approximate the shape of an anatomical structure of the patient. In response to this annotation, server 102 may adjust the position, orientation, and/or shape of the representative structures defined by the atlas to more closely correlate to the representation of the one or more anatomical structures of patient 112. Based on the location of the adjusted position of the structures defined by the atlas, server 102 may provide instructions to IMD 102 via network 504 to deliver electrical stimulation to patient 112.

For example, with respect to FIG. 6B that will be discussed in further detail below, upon receiving annotations, such as annotation 606 via a user interface, anatomical display module 406 of server 102 may adjust the position of atlas-defined structure 602A to more closely align with anatomical structure 604A shown in the patient image. In one example, anatomical display module 406 compares an edge of atlas-defined structure 602A with an edge of the annotation 606. Anatomical display module 406 iteratively moves the atlas-defined structure 602A and determines an error between the atlas-defined structure and the edge of annotation 606 until the distance between the edge of atlas-defined structure 602A and the edge of annotation 606 is minimized. In some examples, anatomical display module 406 iteratively translates and/or rotates the atlas-defined structure 602A with respect to the anatomical structure 604A. Adjustment of the atlas-defined structure 602A may occur independently from other structures defined by the atlas or occur as representative of the adjustment of the entire atlas (or atlas-defined structures from the atlas) with respect to the patient anatomy. In some examples, anatomical display module 406 repeats this translocation in each of an x, y, and z plane. In further examples, the clinician selects a maximum distance or tolerance for the distance between the edge of representative structure 602A and the edge of annotation 606. In this example, anatomical display module 406 iteratively moves the representative structure 602A until the distance between the edge of representative structure 602A and the edge of annotation 606 is less than the tolerance. In some examples, the tolerance may be predefined or selected by the user.

In another example, the anatomical display module 406 of server 102 determines a difference between an edge of atlas-defined structure 602A and an edge of annotation 606. Using an edge of annotation 606 as a reference, anatomical display module 406 roughly aligns atlas-defined structure 602A to anatomical structure 604A and iteratively reduces the scale until atlas-defined structure 602A determines a sufficient match between atlas-defined structure 602A and annotation 606. In some examples, anatomical display module 406 incorporates three-dimensional translation and rotation, so the shape and size of atlas-defined structure 602A is preserved when adjusting its position. In some examples, the clinician manually specifies the amount of scaling anatomical display module 406 performs on atlas-defined structure 602A while adjusting atlas-defined structure 602A. In some examples, anatomical display module 406 compares a mesh of atlas-defined structure 602A with a mesh of annotation 606. For example, anatomical display module 406 compares the sum of squared distances between control points 610 on annotation 606 and the closest corresponding point on the mesh of atlas-defined structure 602A to determine a rotational and translational adjustment to atlas-defined structure 602A.

In another example, the anatomical display module 406 of server 102 receives an annotation 606 via user interface 402 that includes one or more control points 610 from the clinician. The anatomical display module 406 selects one or more points on atlas-defined structure 602A that correspond to the one or more control points 610 from the annotation 606. In one example, annotation 606 and atlas-defined structure 602A possess a plurality of control points spaced a certain distance apart, such as 1 mm, around the perimeter of the respective shape. Anatomical display module 406 determines an error amount between the control points 610 of annotation 606 and corresponding points on anatomical atlas 602A. In some examples, the error amount is determined by computing the least-squares of the distance between the corresponding points. Anatomical display module 406 calculates a potential translation of the atlas-defined structure 602A along six orthogonal directions (e.g., up, down, left, right, forward, or backward) in space, along a first movement amount (e.g., 1 mm), and, for each potential translation, determines the resulting error amount between the control points 610 of annotation 606 and corresponding points on anatomical atlas 602A. Anatomical display module 406 determines a potential translation that provides the greatest reduction in error between control points and then performs the potential translation causing the greatest reduction in error to move the atlas-defined structure 602 in the direction closer to annotation 606 by the first movement amount. Similarly, anatomical display module 406 calculates a potential rotation of the atlas-defined structure 602A in six different directions (e.g., pitch up or down, yaw left or right, roll left or right) along the first movement amount (e.g., 1 mm). For each potential rotation, anatomical display module 406 determines the resulting error amount between the control points 610 of annotation 606 and corresponding points on anatomical atlas 602A. Anatomical display module 406 performs the potential rotation causing the greatest reduction in error to rotate the atlas-defined structure 602 in the direction closer to annotation 606 by the first movement amount.

In some examples, anatomical display module 406 may perform a translation first, and then a rotation, and then iteratively continues this process until no translations or rotations by the first movement amount would cause a reduction in error between the control points of annotation 606 and atlas-defined structure 602A. In other examples, anatomical display module 506 may perform the translation calculations and the rotation calculations from the same starting point and select the one translation or the one rotation that provides the greatest reduction in error between the control points of annotation 606 and atlas-defined structure 602A. Anatomical display module 506 may continue to analyze translations and rotations together from each iterative point and either translate or rotate the atlas-defined structure until no further reduction in error to the annotation can be made. In still other examples, anatomical display module 506 may perform only translations until the error between control points is minimized and then perform rotations until the error between control points is minimized, or vice versa. This procedure may alternate until no translations or rotations by the first movement amount would cause a reduction in error between the control points of annotation 606 and atlas-defined structure 602A.

In one example, anatomical display module 406 continues to iteratively select and perform the translation and/or rotation along the first movement amount that causes the greatest reduction in error until the error amount falls below a deviation threshold, such as a threshold of 1 mm. Then, anatomical display module 406 reduces the first movement amount and deviation threshold and repeats the translation and/or rotation process along the new movement amount that causes the greatest reduction in error until the error amount falls below the new deviation threshold. For example, the reduction in the movement amount and deviation threshold may be halved, e.g., reduced from 1.0 mm to 0.5 mm, or reduced by some other percentage greater than or less than 50 percent from the previous movement amount and deviation threshold. By reducing the movement amount and deviation threshold, the scale of the possible translation and/or rotation of atlas-defined structure 602A is reduces to provide finer movements. Again, the anatomical display module 406 continues to iteratively select and perform the translation and/or rotation along the new movement amount of 0.5 mm that causes the greatest reduction in error until the error amount falls below the deviation threshold of 0.5 mm. The anatomical display module continues to reduce the movement amount and deviation threshold and iteratively translate and rotate the atlas-defined structure 602A until the error amount falls below a maximum deviation. The movement amount and maximum deviation may be preselected, set by clinician input, and/or determined based on the anatomical structures at issue or the size or volumes of the structures. In one example, the movement amount and maximum deviation are 0.1 mm. However, the techniques of the disclosure are suitable for many different movement amounts and maximum deviation amounts, and in some examples, the movement amount and maximum deviation is set to 1.0 mm, 0.3 mm, 1 µm, or even 0.1 µm. In some examples, the movement amount and maximum deviation are equal, while in other examples, the movement amount and maximum deviation are set to different values. In some examples, the movement amount and maximum deviation are reduced by the same amount, while in other examples, the movement amount and maximum deviation are reduced by different amounts, or only one of the movement amount and maximum deviation are reduced. In some examples, the movement amount for the calculated translations and the calculated rotations is the same, while in other examples, one movement amount is used for translations, and while a second movement amount is used for rotations.

In another example, with respect to FIG. 7B that will be discussed in further detail below, anatomical display module 406 of server 102 receives a single annotation 606 in a single plane from a clinician (e.g., annotation 606 of coronal view 702 of FIG. 7B). In this example, annotation 606 provides sufficient information to anatomical display module 406 such that anatomical display module 406 may perform a translation of the atlas-defined structure 602A along the single plane of the annotation according to the techniques described above.

Figure 7A:
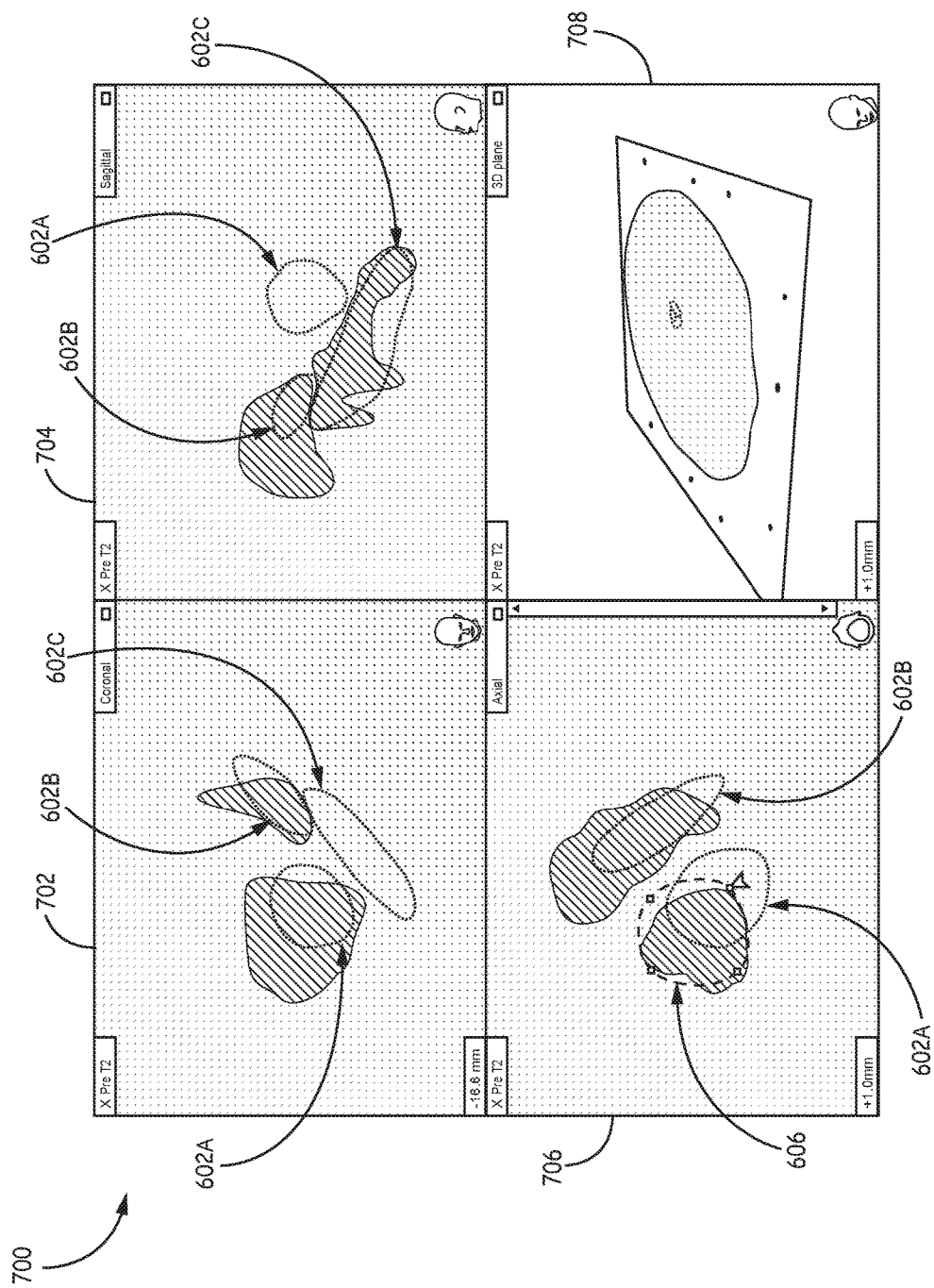
FIGS. 7A-7B are illustrations of an example user interface and user annotation to align an atlas-defined anatomical structure over a representation of an anatomical region of the patient according to the techniques of the disclosure.
Figure 7B:
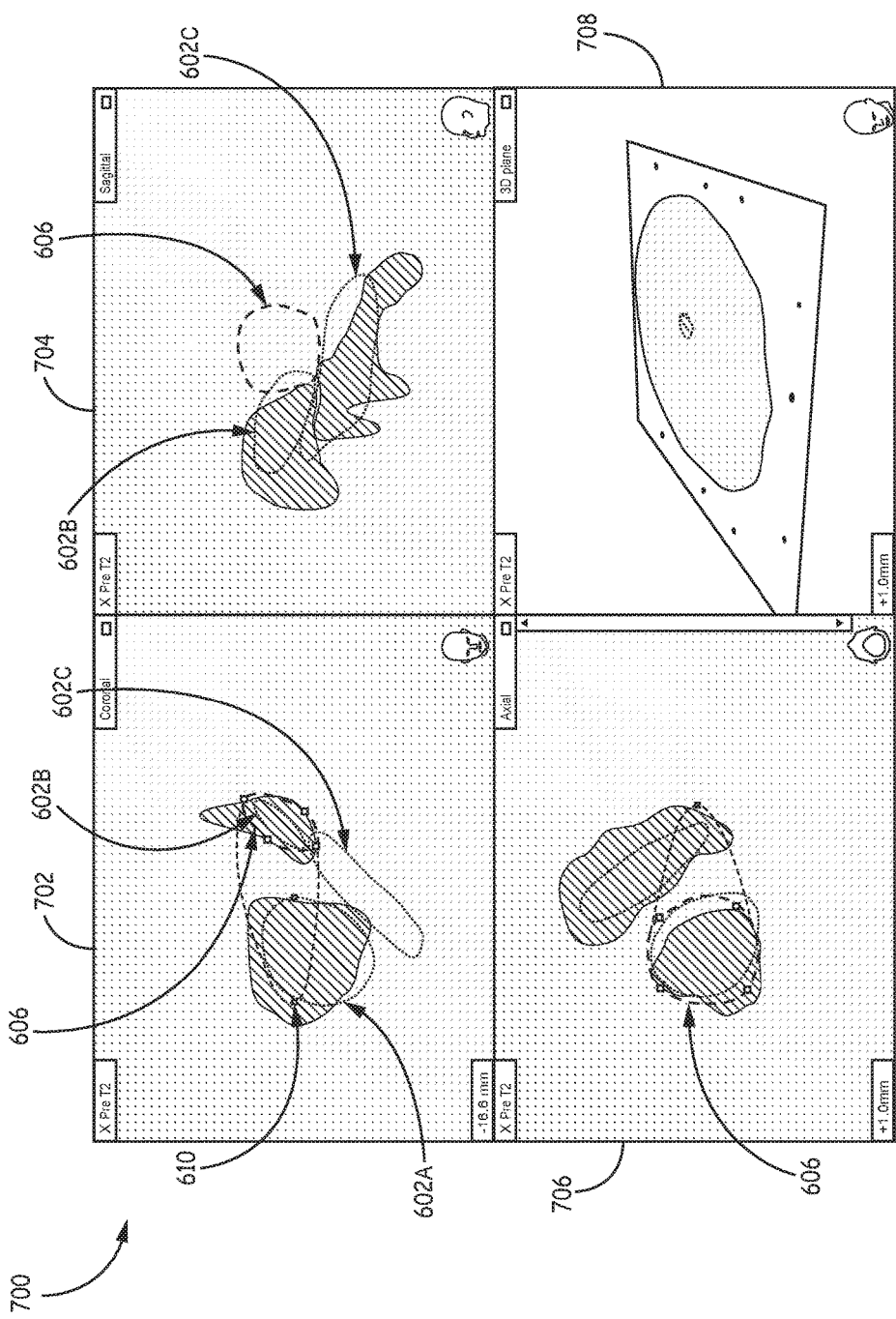

In another example, anatomical display module 406 of server 102 receives a first annotation 606 in a first plane (e.g., annotation 606 of coronal view 702 of FIG. 7B) and a second annotation 606 in a second plane (e.g., annotation 606 of sagittal view 704 of FIG. 7B). In this example, annotations 606 provided in two different planes (e.g., orthogonal planes) provide sufficient information to anatomical display module 406 such that anatomical display module 406 may perform a rotation, or a rotation and translation, of the atlas-defined structure 602A along the two different planes according to the techniques described above. In other words, two annotations in different planes may allow enough information from the annotations to allow for more fine tuning of the movement of the atlas-defined structure than is possible with only a single annotation in one place.

In yet a further example, anatomical display module 406 of server 102 receives a first annotation 606 in a first plane (e.g., annotation 606 of coronal view 702 of FIG. 7B), a second annotation 606 in a second plane (e.g., annotation 606 of sagittal view 704 of FIG. 7B), and a third annotation 606 in a third plane (e.g., annotation 606 of coronal view 706 of FIG. 7B). In this example of annotations in three different planes, annotations 606 provide sufficient information to anatomical display module 406 such that anatomical display module 406 may rotate, translate, resize, reshape, reform, or warp the atlas-defined structure 602A according to the techniques described above. In some examples, anatomical display module 406 may receive more than three annotations, either in more than three planes and/or for additional structures of the atlas. Anatomical display module 406 may provide more accurate adjustment of the atlas with more annotations provided by the user.

In one example, anatomical display module 406 resizes, reshapes, reforms, or warps the atlas-defined structure 602A by receiving the first annotation 606 in a first plane (e.g., annotation 606 of coronal view 702 of FIG. 7B), the second annotation 606 in a second plane (e.g., annotation 606 of sagittal view 704 of FIG. 7B), and the third annotation 606 in a third plane (e.g., annotation 606 of coronal view 706 of FIG. 7B). In this example, the three annotations provide sufficient information such that anatomical display module 406 creates a three-dimensional annotation by interpolating the information provided from the three annotations 606. The anatomical display module 406 generates a plurality of control points spaced a certain distance apart, such as 1 mm, around the surface mesh of the interpolated, three-dimensional annotation. Further, the anatomical display module 406 assigns one or more control points to the surface mesh of the three-dimensional atlas-defined structure 602. The anatomical display module 406 selects one or more points on the three-dimensional atlas-defined structure 602 that correspond to the one or more control points 610 from the interpolated, three-dimensional annotation 606. Anatomical display module 406 determines an error amount between the control points 610 of annotation 606 and corresponding points on anatomical atlas 602A. Anatomical display module 406 resizes, reshapes, reforms, or warps the atlas-defined structure 602A to more closely align with the interpolated, three-dimensional annotation 606 by iteratively walking each of the control points of three-dimensional annotation 606 toward a corresponding control point of the interpolated, three-dimensional annotation 606, using the techniques described above. Accordingly, anatomical display module 406 moves the control points of the atlas-defined structure 602A to adjust the shape of the surface mesh of the atlas-defined structure 602A, thereby resizing, reshaping, reforming, or warping portions of atlas-defined structure 602A to more closely align with the anatomical structures of brain 120 of patient 112.

The architecture of system 500 illustrated in FIG. 5 is shown as an example. The techniques as set forth in this disclosure may be implemented in the example system 500 of FIG. 5, as well as other types of systems not described specifically herein. Nothing in this disclosure should be construed so as to limit the techniques of this disclosure to the example architecture illustrated by FIG. 5.

Figure 6A:
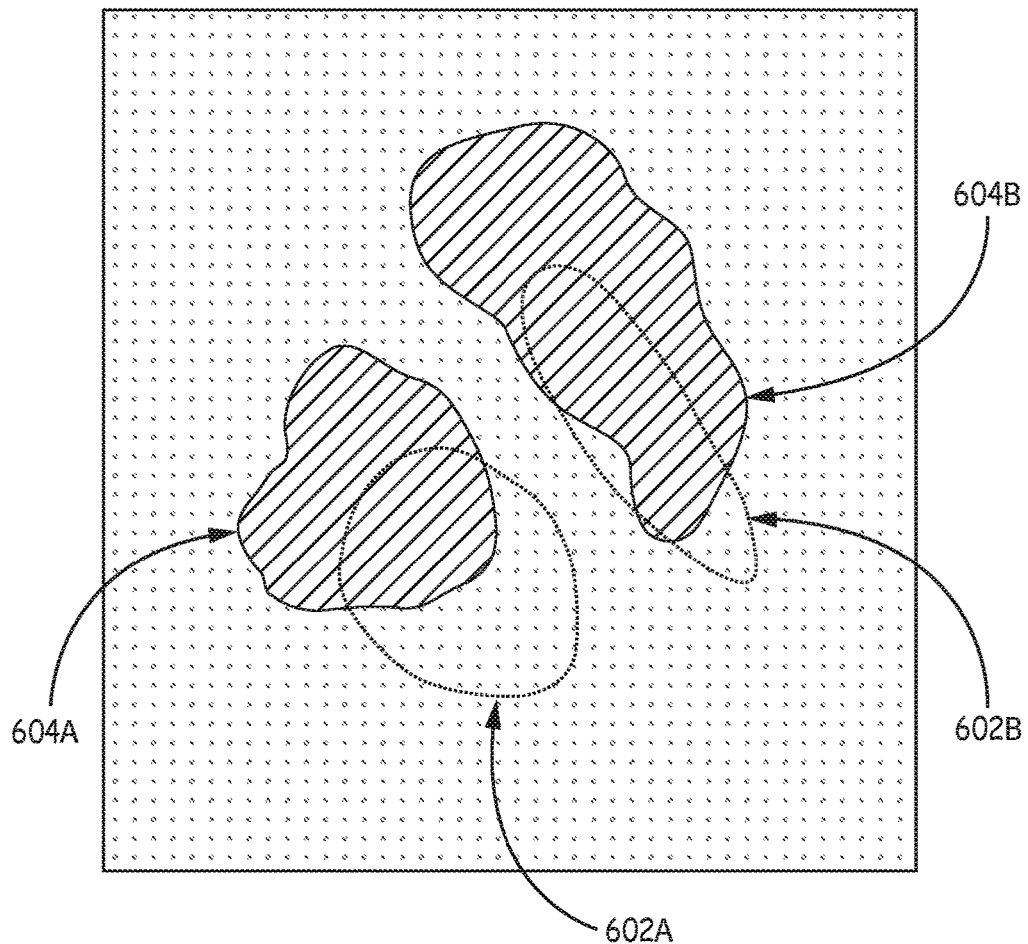
FIGS. 6A-6C are illustrations of an example user interface and user annotation to align an atlas-defined anatomical structure over a representation of an anatomical region of the patient according to the techniques of the disclosure.
Figure 6B:
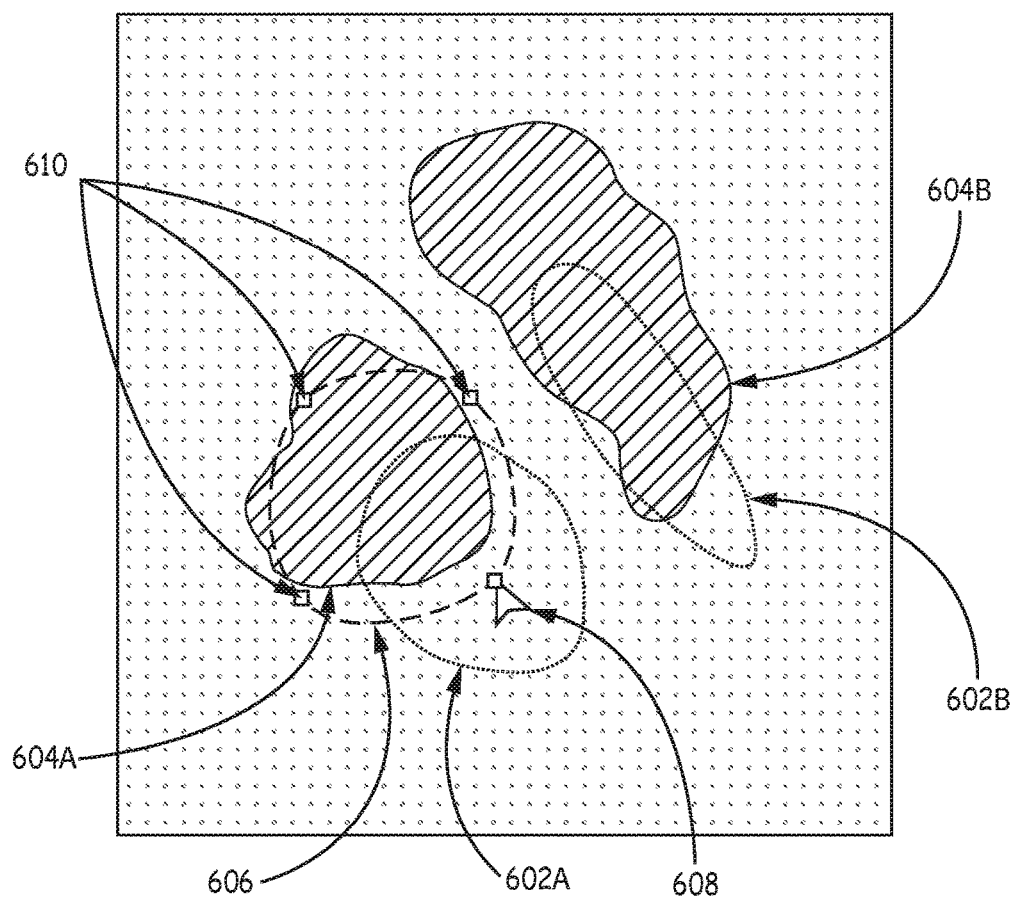
Figure 6C:
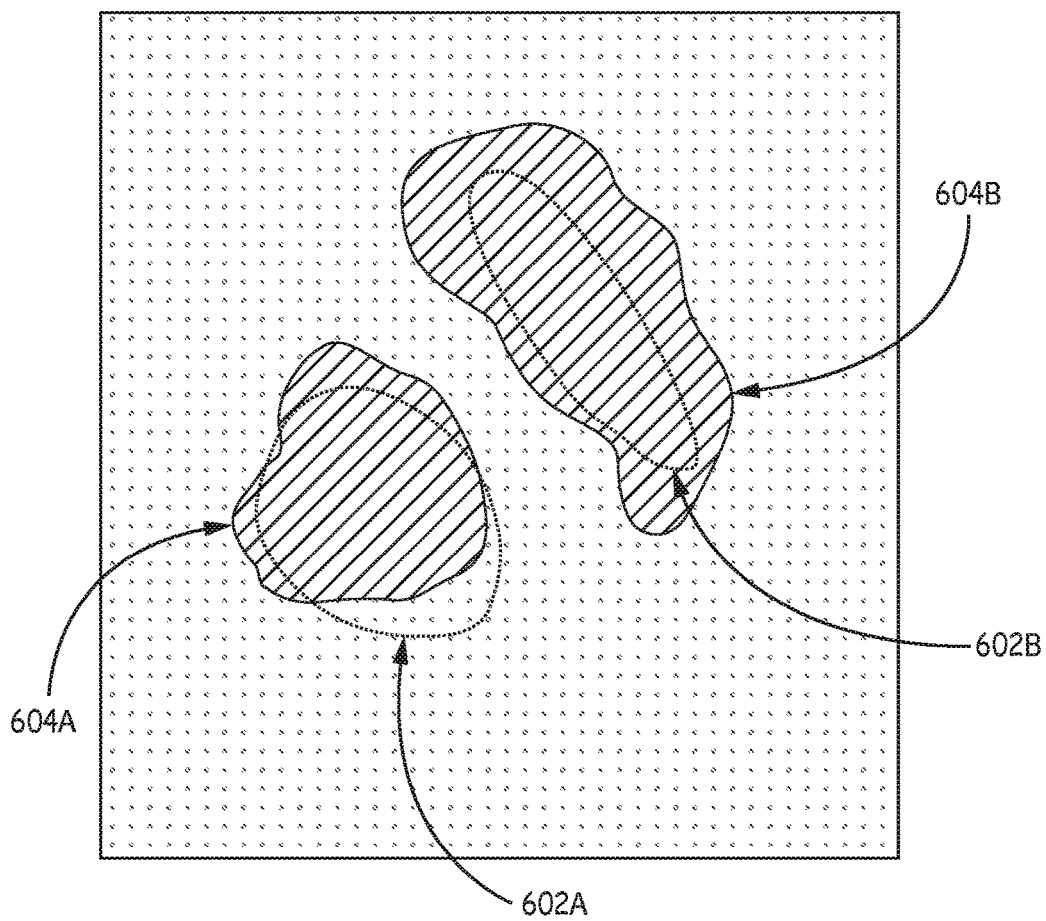

FIGS. 6A-6C are illustrations of an example user interface and user annotations that align an atlas-defined anatomical structure over a representation of an anatomical region of the patient according to the techniques of the disclosure. For convenience, FIGS. 6A-6C are described with respect to networked server 102 of FIG. 4. However, any system or device may provide similar user interfaces. FIGS. 6A-6C show a single 2D view of anatomical structures 604A and 604B and atlas-defined structures 602A and 602B. As described further below, annotations may be made in two or more 2D views in order to adjust atlas-defined structures to anatomical structures of the patient.

With respect to FIG. 6A, the example user interface includes anatomical structures 604A and 604B that are in a representation, or image, of the patient anatomy from patient 112. The user interface further includes atlas-defined structures 602A and 602B defined by an atlas. Because atlas-defined structures 602A and 602B are defined by the atlas, they may not accurately reflect the actual location of anatomical structures 604A and 604B of patient 112. As shown in FIG. 6A, atlas-defined structures 602A and 602B differ slightly in location from anatomical structures 604A and 604B. Although anatomical structures 604A and 604B are shown by dotted lines, the dotted lines are provided to illustrate the anatomical structures that would be identified by a user, such as a clinician. The dotted lines of anatomical structures 604A and 604B may thus not be shown in the user interface.

With respect to FIG. 6B, the example user interface provides an annotation 606 for manipulation by a clinician. The user interface may present a default annotation 606 upon request by the user. In other examples, the user may select a free-hand annotation tool that allows the user to draw or outline the desired annotation representing the anatomical structure of the patient anatomy. In the example of FIG. 6B, the clinician manipulates annotation 606 to more accurately reflect the shape and location of anatomical structure 604A. In this example, the annotation is intended to correspond to an adjustment of atlas-defined structure 602A. For example, server 102 may automatically correlate atlas-defined structure 602A with anatomical structure 604A because atlas-defined structure 602A is the closest atlas structure to the annotation 606. However, the annotation may correspond to any atlas-defined structure depicted by the user interface or selected by the user. In some examples, the annotation 606 includes one or more control points 610 located on annotation 606. In one example, the clinician may, using cursor 608, select a control point 610 and drag the control point to an edge of the anatomical structure 604A. The clinician may repeatedly adjust the position of each of the control points 610 to outline anatomical structure 602A to which the clinician would like to move atlas-defined structure 602A. In other examples, annotation 606 may be drawn free-hand by the user or the user may generate a plurality of points around the outline of anatomical structure 604A for the system to connect as the annotation 606.

With respect to FIG. 6C, upon receiving annotation 606 from the user and the user interface, anatomical display module 406 of server 102 adjusts the position of atlas-defined structure 602A to more closely align with anatomical structure 604A. In one example, anatomical display module 406 compares an edge of atlas-defined structure 602A with an edge of the annotation 606. Anatomical display module 406 iteratively moves the representative structure 602A until the distance between the one or more edges of representative structure 602A and the edges of annotation 606 is minimized. For example, anatomical display module 406 may move the atlas-defined structure 602 in a first direction until the distance between the edges are minimized and repeat this process in one or more additional directions different than the first direction. These other directions may be orthogonal, but other directions may be pre-selected or selected based on an analysis of the positions of annotation 606 and atlas-defined structure 602A. In some examples, anatomical display module 406 repeats this translocation in each of an x, y, and z plane. As illustrated by FIG. 6C, in response to annotation 606, server 102 has adjusted the position of representative structures 602A and 602B to more closely align with anatomical structures 604A and 604B. Although the annotation process has been described for anatomical structure 604A, an annotation may alternatively or additional provided for anatomical structure 604B. If multiple annotations are provided for respective atlas-defined structures (e.g., atlas-defined structures 602A and 602B), anatomical display module 406 may translate and/or rotate the atlas-defined structures until the collective distances between edges of the atlas-defined structures and anatomical structures are minimized.

Accordingly, the techniques of the disclosure may allow for a clinician to more accurately correlate atlas-defined structures defined by an anatomical atlas to anatomical structures of the patient. In doing so, the clinician may more accurately implant a lead to the desired location and/or deliver therapy to the targeted anatomical structures of the patient. Such targeted therapy may allow a clinician to deliver more precise control over which areas of the brain receive therapy. Further, the techniques may allow the clinician to partially or completely disregard the electrode locations and focus on selecting the structures that need to be stimulated to treat the patient may decrease clinician time and confusion in configuring the electrical stimulation, and increase therapy efficacy.

The user interface illustrated in FIGS. 6A-6C is shown as an example. The techniques as set forth in this disclosure may be implemented with the example user interface of FIGS. 6A-6C, as well as other types of user interfaces not described specifically herein. Nothing in this disclosure should be construed so as to limit the techniques of this disclosure to the example user interface illustrated by FIGS. 6A-6C.

FIGS. 7A-7B are illustrations of an example user interface and user annotation to align an atlas-defined anatomical structure over a representation of an anatomical region of the patient according to the techniques of the disclosure. For convenience, FIGS. 7A-7C are described with respect to server 102 of FIG. 4. In the example of FIG. 7A, user interface 700 includes different orthogonal views such as a coronal view 702, a sagittal view 704, an axial view 706, and a three-dimensional view 708. As described above with respect to FIGS. 6A-6C, user interface 700 displays representative structures 602A-602C overlaid on an anatomical representation of a patient 112. Axial view 706 may be similar to the 2D views of FIGS. 6A-6C.

Each of coronal view 702, sagittal view 704, and axial view 706 depicts the same three-dimensional anatomical region of brain 120 of patient 112, according to a two-dimensional coronal, sagittal, and axial slice of brain 120, respectively. With respect to coronal view 702 of FIG. 7A, user interface 700 displays a coronal representation of the anatomical region of brain 120 of patient 112. User interface 700 further overlays representative structures 602A-602C across the coronal view of brain 120. Further, user interface 700 displays an annotation 606 across the coronal view of brain 120. Sagittal view 704 depicts the same anatomical region of brain 120 of patient 112 as coronal view 702, but according to a sagittal slice of brain 120. Sagittal view 704 further depicts a sagittal view of representative structures 602A-602C and annotation 606. Similarly, axial view 706 depicts the same anatomical region of brain 120 of patient 112 as coronal view 702, but according to an axial slice of brain 120. Axial view 706 further depicts an axial view of representative structures 602A-602C and annotation 606. Three-dimensional view 708 depicts a three-dimensional view of the anatomical region of patient 112 and includes three-dimensional representations of representative structures 602A-602C depicted in coronal view 702, sagittal view 704, and axial view 706.

With respect to FIG. 7B, the clinician manipulates annotation 606 (labeled in axial view 706) to more accurately reflect the shape of anatomical structure 604A. In this example, the annotation corresponds to an adjustment of atlas-defined structure 602A. However, annotation 606 may correspond to any atlas-defined structure depicted by the user interface. In some examples, the annotation 606 includes one or more control points 610. In one example, the clinician may, using cursor 608, select control point 610 and drag the control point to an edge of the atlas-defined structure 602A. The clinician may repeatedly adjust the position of each of the control points 610 to outline atlas-defined structure 602A.

In other examples, user interface 700 provides a tracing tool that allows a clinician to provide an annotation by tracing a free-form outline of an anatomical structure of patient 112. In some examples, user interface 700 provides a button to allow a clinician to select a closed contour annotation, such as an ellipse, rectangle, or circle, or an open-contour annotation, such as a straight or elliptical line segment. In further examples, user interface 700 provides a scaling tool that allows the clinician to increase or decrease the size of the annotation. In some examples, the scaling tool is a slider button that allows a clinician to adjust the scale of the annotation by clicking and dragging a button.

In further examples, user interface provides a "lasso" type tool that attempts to outline an anatomical structure based on analysis of the representation of the anatomical region of patient 112, such as determining structures by detecting differences in contrast or lines in the representation.

In some examples, the clinician adjusts the annotation in a single view, such as within coronal view 702 only. In other examples, the clinician adjusts the annotation in multiple views, such as within both coronal view 702 and axial view 706. In some examples, user interface 700 receives a selection, by the clinician, of a representative structure, such as representative structure 602A, with which to associate the annotation. In other examples, user interface 700 associates the annotation with a representative structure determined to be closest to the annotation. In some examples, the user interface 700 depicts a preview of the adjustment to the annotation. In the example of FIG. 7B, this preview is depicted as a dotted line. The user interface 700 presents the preview to the clinician, and upon receiving confirmation from the clinician that the previous is acceptable, adjusts the annotation accordingly. After user interface 700 receives the adjusted annotation, it may provide information describing the annotation to server 102 to adjust the position of representative structures 602A-602C, as described above.

Although annotation 606 is shown in axial view 706, the user may provide additional annotations in different views 702 and 704, for example. Each annotation provided in the respective view may allow the system to more accurately adjust the atlas structures to the appropriate structures of the patient. Although atlas-defined structures 602A, 602B, and 602C are shown in each of the views 702, 704, and 706 to illustrate the different orthogonal view of the 3D structures, the annotation may not have three dimensions. In other words, the annotations in each 2D view may only be used in that view. Additional annotations may be provided in different views to further refine the adjustments to atlas-defined structures. 3D view 708 may display three-dimensional views of the atlas-defined structures in relation to a 2D plane of patient anatomy (shown in FIG. 7B) or a 3D representation of the patient anatomy. The system may receive user input rotating 3D view 708 as desired by the user. As described herein, the system may adjust the atlas-defined structures to minimize errors between the annotations (e.g., annotation 606) and the respective atlas-defined structures.

The user interface illustrated in FIGS. 7A-7B is shown as an example. The techniques as set forth in this disclosure may be implemented with the example user interface of FIGS. 7A-7B, as well as other types of user interfaces not described specifically herein. Nothing in this disclosure should be construed so as to limit the techniques of this disclosure to the example user interface illustrated by FIGS. 7A-7B.

Figure 8:
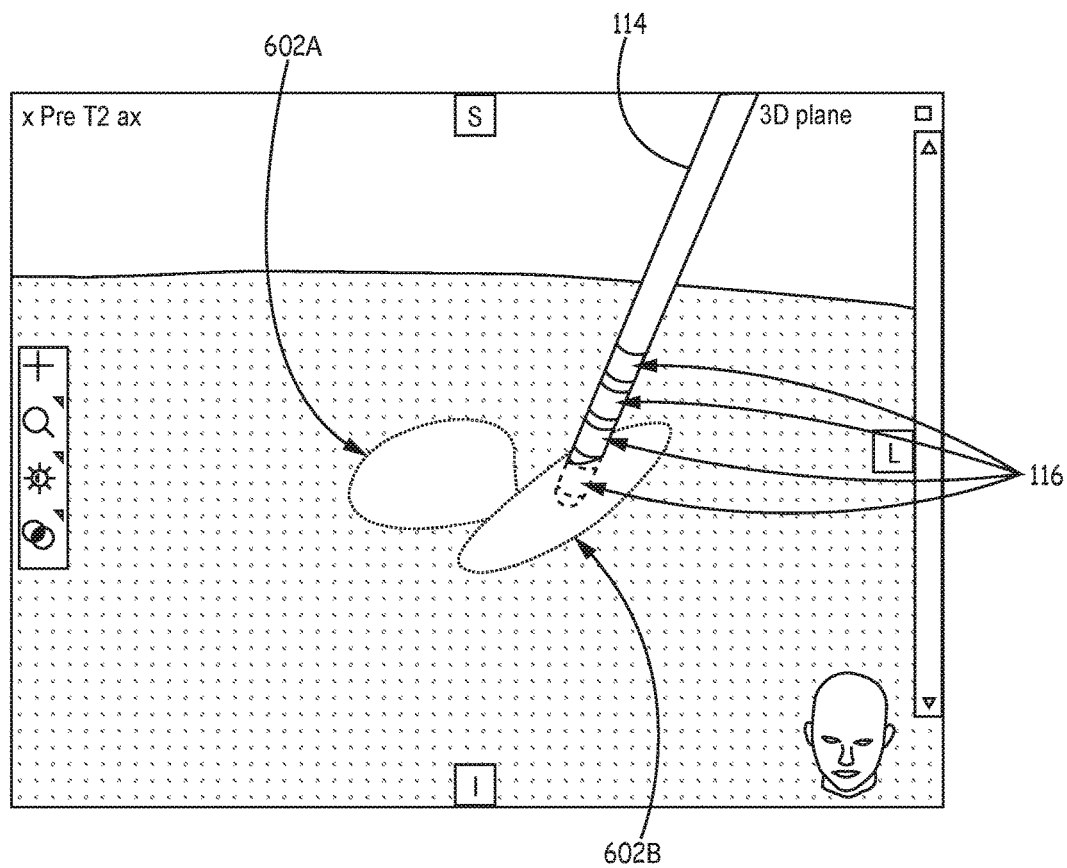
FIG. 8 is an illustration of an example atlas-defined structure over an anatomical region of a patient according to the techniques of the disclosure.

FIG. 8 is an illustration of an example atlas-defined structure over an anatomical region of a patient according to the techniques of the disclosure. In the example of FIG. 8, upon receiving an annotation from the clinician, server 102 adjusts the position of representative structure 602A to more closely align with anatomical structure 604A. Server 102 generates and transmits commands to IMD 106 to deliver therapy to a target area of patient 112 via lead 114 and electrodes 116 based on the adjusted position of the representative structure 602A.

The illustration of FIG. 8 is shown as an example. The techniques as set forth in this disclosure may be implemented in the example illustration of FIG. 8, as well as other types of implementations not described specifically herein. Nothing in this disclosure should be construed so as to limit the techniques of this disclosure to the example architecture illustration of FIG. 8.

Figure 9:
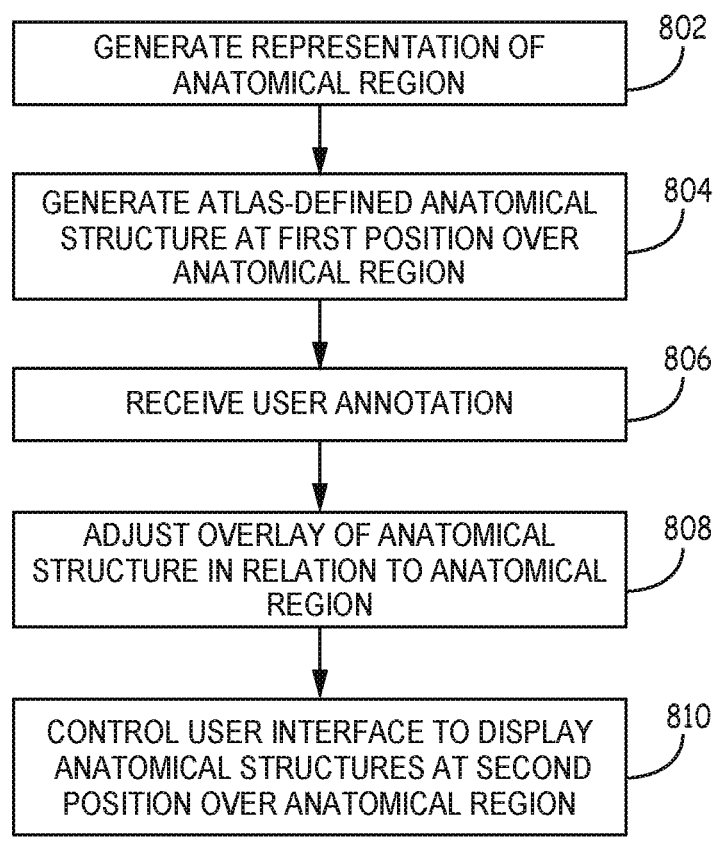
FIG. 9 is a flowchart providing an example process according to the techniques of the disclosure.

FIG. 9 is a flowchart providing an example operation according to the techniques of the disclosure. For convenience, FIG. 9 is described with respect to the components and circuitry of server 102 of FIG. 4. In the example of FIG. 9, anatomical display module 406 generates a representation of an anatomical region of patient 112 (802). In some examples, the anatomical region is the brain 120 of patient 112. Atlas overlay module 404 retrieves one or more structures of anatomical atlases 412 stored in memory 411 and generates an atlas-defined anatomical structure at a first position over the anatomical region (804).

Annotation module 414 may overlay an annotation over the representation of the one or more anatomical structures of patient 112. Annotation module 414 may generate the annotation at the request of a user. Annotation module 414 may receive user input defining the annotation (e.g., user annotation) such that the user annotation may closely approximate one or more of the structures overlaid on the representation of the patient. Annotation module 414 may, via user interface 402, receive adjustments to the annotation from a clinician (806). For example, the annotation may include one or more "control points" or "adjustment handles" that are selectable or movable by user input. The clinician may, via user interface 402, click and drag the control points on the annotation to change the shape of the annotation. In this manner, the clinician may manipulate the shape of the annotation to approximate the shape of an anatomical structure of the patient.

In response to receiving the annotation, atlas overlay module 404 adjusts the position of the atlas-defined structures defined by atlases 412 with respect to the representation of the one or more anatomical structures of patient 112 in accordance with the received annotation (808). As discussed herein, atlas overlay module 404 may adjust the position of the atlas-defined structure by iteratively moving the atlas-defined structure with respect to the annotation until the distances between the edges of the atlas-defined structure and the annotation are minimized. Atlas overlay module 404 may translate and/or rotate the atlas-defined structures in different planes. This adjustment to the atlas-defined structures may involve individual and separate movement of each atlas-defined structure or the adjustment of one atlas-defined structure may correspondingly move the entire atlas or all atlas-defined structures by using the single atlas-defined structure as a reference. Further discussion regarding the translation and/or rotation of the atlas-defined structure is provided herein with respect to FIGS. 6, 7, and 12. Anatomical display module 406 may then control user interface 402 to display the adjusted anatomical structures at a second position over the anatomical region (810).

The operation illustrated in FIG. 9 is shown as an example. The techniques as set forth in this disclosure may be implemented in the example operation of FIG. 9, as well as other types of systems not described specifically herein. Nothing in this disclosure should be construed so as to limit the techniques of this disclosure to the example architecture illustrated by FIG. 9.

Figure 10:
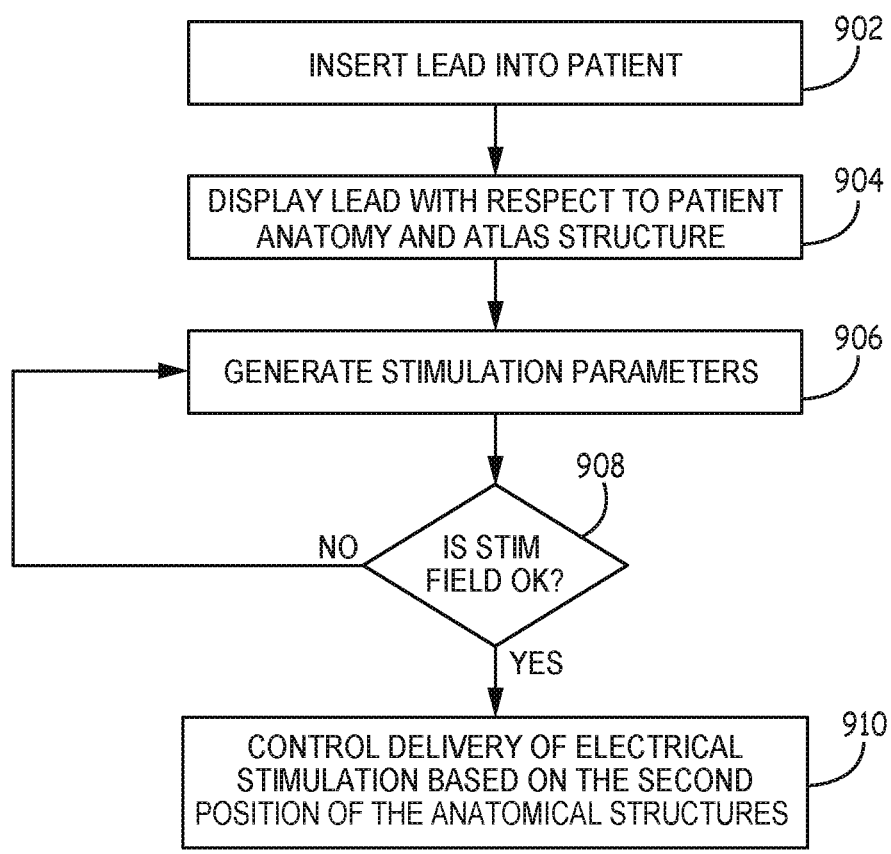
FIG. 10 is a flowchart providing an example process according to the techniques of the disclosure.

FIG. 10 is a flowchart providing an example operation according to the techniques of the disclosure. For convenience, FIG. 10 is described with respect to server 102 of FIG. 4. As shown in FIG. 10, a lead is implanted into patient 112 (902). In some examples, the lead is lead 114 of FIG. 1 and is configured to stimulate the brain 120 of patient 112. Using information locating the lead within patient anatomy, anatomical display module 406 may display, via user interface 402, the lead with respect to a representation of the anatomy of the patient 112 (904). The representation of the anatomy may include atlas-defined structures that have been adjusted to correlate with patient anatomy as described in FIG. 9. Therefore, the user may visualize one or more atlas-defined structures along with lead electrodes and/or possible stimulation fields that can be generated by the electrodes. The user may also select one or more atlas-defined structures desired to be affected by stimulation or avoided by the stimulation. Using this information, server 102 generates stimulation parameters (e.g., in a process similar to the operation of FIG. 9 (906). The stimulation parameters may define a representation of the stimulation field that may be generated using the stimulation parameters. In some examples, server 102 performs a check of the stimulation parameters to determine whether the stimulation parameters are within acceptable stimulation ranges, such as the stimulation field treating and/or avoiding desired anatomical regions of the patient (908). If the stimulation field is not acceptable ("NO" branch of block 908), server 102 regenerates stimulation parameters such that the stimulation parameters are within acceptable ranges (906). At this point the user may also request changes to the stimulation parameters. If the stimulation parameters and resulting stimulation field are acceptable ("YES" branch of block 908), server 102 controls delivery, by IMD 106, of electrical stimulation based on stimulation parameters (910).

The operation illustrated in FIG. 10 is shown as an example. The techniques as set forth in this disclosure may be implemented in the example operation of FIG. 10, as well as other types of systems not described specifically herein. Nothing in this disclosure should be construed so as to limit the techniques of this disclosure to the example architecture illustrated by FIG. 10.

Figure 11:
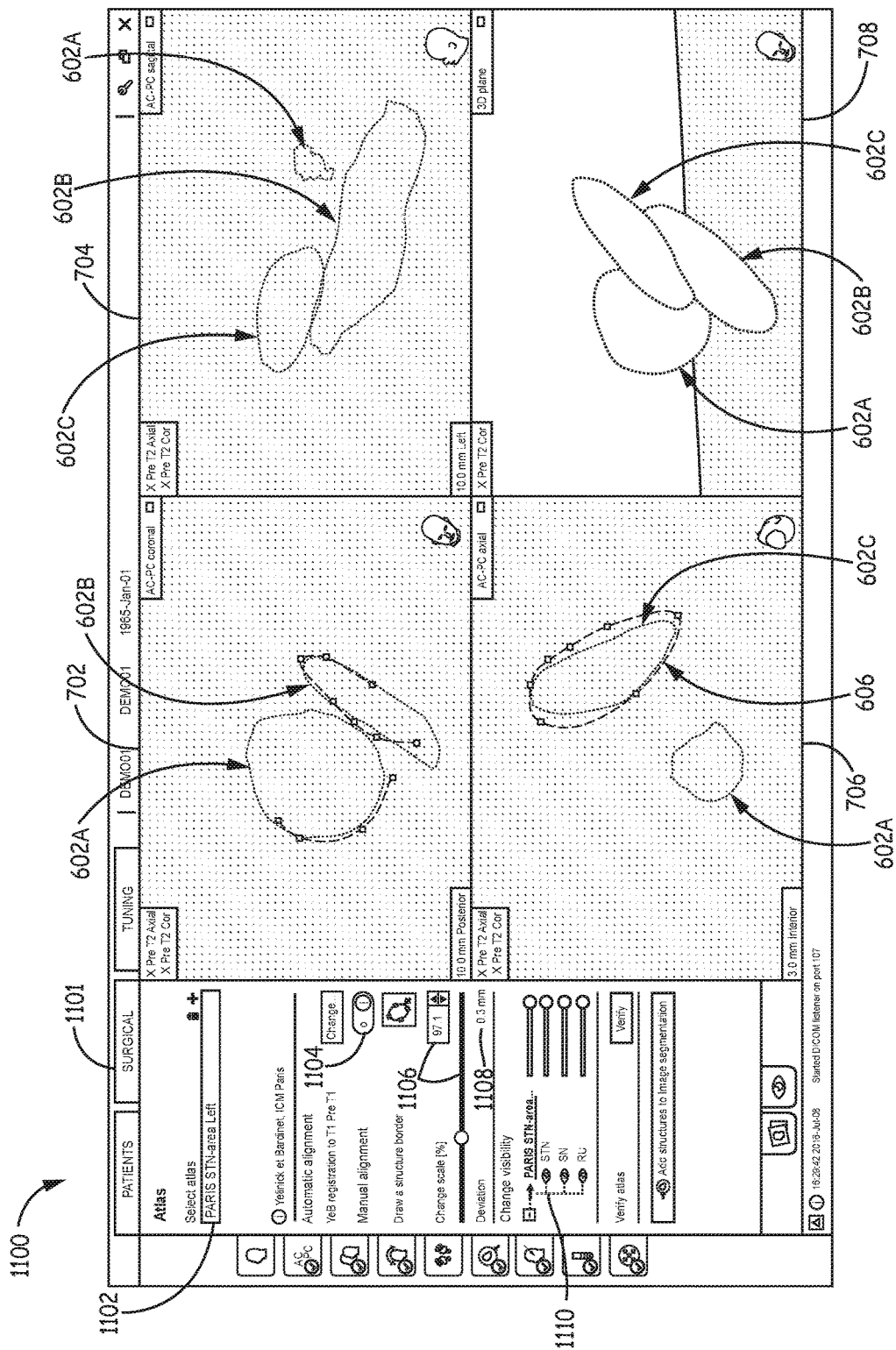
FIG. 11 is an illustration of an example user interface for facilitating user adjustment of the position of one or more structure of an anatomical atlas to patient anatomy.

FIG. 11 is an illustration of an example user interface 1100 for facilitating user adjustment of the position of one or more structure of an anatomical atlas to patient anatomy. As depicted in FIG. 11, user interface 1100 includes a user control panel 1101 and different orthogonal views of brain 120 of patient 112, such as a coronal view 702, a sagittal view 704, an axial view 706, and a three-dimensional view 708.

User control panel 1101 provides various tools and options that are selectable and allow a clinician to control and adjust the representation of brain 120 of patient 112 displayed by coronal view 702, sagittal view 704, axial view 706, and three-dimensional view 708. In one example, user interface 1100 includes an atlas selection tool 1102. The atlas selection tool 1102 provides a selection interface (e.g. a drop-down menu or text field) from which user interface 1100 may receive, from a clinician, a selection of an atlas-defined structure 602 for adjustment according to the techniques of the disclosure. In the example of FIG. 11, the user interface 1100 receives a selection of atlas-defined structures 602A, 602B, or 602C from a clinician via the atlas selection feature, or via input from a mouse click on the desired atlas displayed by coronal view 702, sagittal view 704, axial view 706, and three-dimensional view 708.

In the example of FIG. 11, control panel 1101 further includes a manual alignment tool 1104. Manual alignment tool 1104 allows user interface 1100 to receive a selection of an automatic alignment option and a manual alignment option from a clinician. When the control panel 1101 receives a selection of the automatic alignment option from the clinician, the server 102 attempts to automatically position atlas-defined structures 602 over the corresponding representation of the anatomical region of the patient. When the control panel 1101 receives a selection of the manual alignment option from the clinician, in accordance with the techniques of the disclosure, user interface 1100 further receives an annotation from the clinician on one or more of coronal view 702, sagittal view 704, axial view 706 to provide guidance to the server 102 such that server 102 adjusts the overlay of the atlas-defined anatomical structure over the anatomical region of the brain 120 of patient 112.

In the example of FIG. 11, control panel 1101 further includes a scaling tool 1106. Scaling tool 1106 allows the clinician to adjust the size (e.g., volume) or scale of the atlas-defined structure 602 displayed by coronal view 702, sagittal view 704, axial view 706, and three-dimensional view 708. In the example of FIG. 11, scaling tool 1106 may be a slider bar that is movable by a clinician to grossly adjust the scale of the atlas-defined structure 602. For precision adjustment of the scale of the atlas-defined structure 602, scaling tool 1106 may also, or alternatively, include a scaling field box configured to receive a numerical input from the clinician and/or arrow buttons of the scaling field box to increase and/or decrease the scaling value.

In the example of FIG. 11, control panel 1101 further includes a deviation tool 1108. Deviation tool 1108 receives input from the clinician setting the maximum deviation as used by anatomical display module 406 of server 102 to determine how closely to match the atlas-defined structure 602 to the annotation 606 provided by the clinician. In the example of FIG. 11, the maximum deviation is set to 0.3 mm. However, the techniques of the disclosure are suitable for many different maximum deviation amounts, and in some examples, the maximum deviation is set to 1 mm, 0.1 mm, 1 μm, or 0.1 μm. In some examples, deviation tool 1108 may only indicate the maximum deviation, and/or current deviation threshold, instead of receiving user input.

In the example of FIG. 11, control panel 1101 further includes a transparency tool 1110. Transparency tool 1110 allows user interface 1100 to receive, from the clinician, a selection of the transparency of the atlas-defined structures 602. In the example of FIG. 11, transparency tool 1110 displays the transparency of atlas-defined structures 602 in a tree form for enhanced control. For example, transparency tool 1110 may receive individual input for each atlas-defined structure such that user interface 1100 may receive, from the clinician, a selection of the transparency of each individual atlas-defined structure 602A, 602B, or 602C (e.g., each leaf of the tree), or a selection of the transparency of all of the atlas-defined structures 602 together (e.g., a branch of the tree). Furthermore, the example transparency tool 1110 of FIG. 11 allows user interface 1100 to receive, from the clinician, a selection of the transparency via an adjustment to a slider bar. However, in other examples, transparency tool 1110 may be implemented in other schemes, such as via an input box, or as buttons.

The user interface 1100 illustrated in FIG. 11 is shown as an example. The techniques as set forth in this disclosure may be implemented in the example user interface 1100 of FIG. 11, as well as other types of user interfaces not described specifically herein. For example, a user interface according to the techniques of the disclosure may include one or more of the tools provided by control panel 1101, or different tools, not expressly discussed herein, that provide similar functionality. Nothing in this disclosure should be construed so as to limit the techniques of this disclosure to the example architecture illustrated by FIG. 11.

Figure 12:
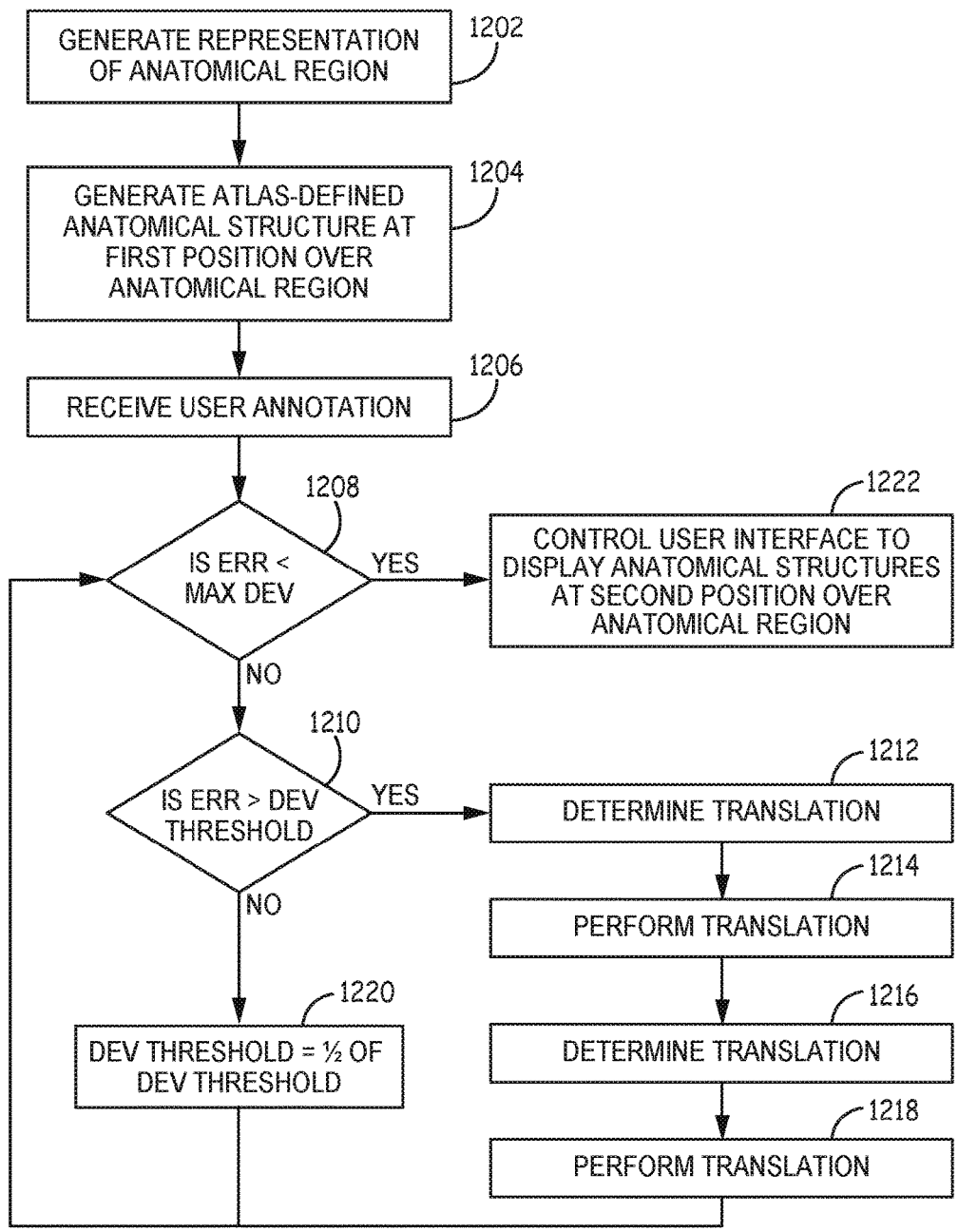
FIG. 12 is a flowchart providing an example process according to the techniques of the disclosure.

FIG. 12 is a flowchart providing an example process according to the techniques of the disclosure. For convenience, FIG. 12 is described with respect to the components and circuitry of server 102 of FIG. 4. In the example of FIG. 12, anatomical display module 406 generates a representation of an anatomical region of patient 112 (1202). In some examples, the anatomical region is the brain 120 of patient 112. Atlas overlay module 404 retrieves one or more structures of anatomical atlases 412 stored in memory 411 and generates an atlas-defined anatomical structure at a first position over the anatomical region (1204). In some examples, two or more atlas-defined structures may be generated at the same time.

Annotation module 414 may overlay an annotation over the representation of the one or more anatomical structures of patient 112 (1206). Annotation module 414 may generate the annotation at the request of a user. Annotation module 414 may receive user input defining the annotation (e.g., user annotation) such that the user annotation may closely approximate one or more of the structures overlaid on the representation of the patient. Annotation module 414 may, via user interface 402, receive adjustments to the annotation from a clinician. For example, the annotation may include one or more "control points" or "adjustment handles" on an outer surface or outline of the annotation that are selectable or movable by user input. The clinician may, via user interface 402, click and drag the control points on the annotation to change the shape of the annotation. In this manner, the clinician may manipulate the shape of the annotation to approximate the shape of an anatomical structure of the patient as shown in the user interface.

In response to receiving the annotation, atlas overlay module 404 adjusts the position of the one or more atlas-defined structures defined by atlases 412 with respect to the representation of the one or more anatomical structures of patient 112 in accordance with the received annotation. In one example, the anatomical display module 406 selects one or more points on atlas-defined structure 602A that correspond to the one or more control points 610. Anatomical display module 406 determines an error amount between the corresponding control points 610 of annotation 606 and points on anatomical atlas 602A (1208). In some examples, anatomical display module 406 determines the error amount by computing the least-squares of the distance between the corresponding points of annotation 606 and atlas-defined structure 602A. If anatomical display module 406 determines that the error is greater that a maximum deviation ("NO" branch of block 1208), then anatomical display module 406 determines whether the error amount is greater than a deviation threshold amount (1210). If the error is greater than the deviation threshold ("YES" branch of block 1210), anatomical display module 406 determines the error amount for a translation of the atlas-defined structure 602A in each orthogonal direction, such as up, down, left, right, forward, or backward, along a first movement amount (e.g. 1 mm) (1212). Anatomical display module 406 performs the translation along the first movement amount in the direction that provides the greatest reduction in error (e.g., provides the best match of the annotation to the atlas-defined structure for any of the movement directions) (1214). Anatomical display module 406 then determines the error amount for rotation of the atlas-defined structure 602A in each rotational direction (e.g., pitch up and down, yaw left and right, roll left and right), along the first movement direction (1216). In some examples, anatomical display module 406 iteratively calculates the rotation around one or more control points of the atlas-defined structure 602A. In other examples, anatomical display module 406 iteratively calculates the rotation around one or more control points of the annotation 606. In other examples, anatomical display module 406 calculates the rotation around the centroid of the atlas-defined structure 602A. Anatomical display module 406 then performs the rotation in the direction that provides the greatest reduction in error (1218).

As discussed herein, anatomical display module 406 may utilize different approaches with respect to the order of translations and rotations through the iterations of movement in order to attempt to move the atlas-defined structure closer to the user provided annotation. For example, anatomical display module 406 may determine a rotation in the direction that provides the greatest reduction in error and perform the rotation prior to determining a translation in the direction that provides the greatest reduction in error and performing the translation. In another example, anatomical display module 406 determines the error amount for both a translation and a rotation, and performs one of the translation and rotation, but not both, that provides the greatest reduction in error as compared to each of the calculated translations and rotations, before iteratively calculating the next translation and/or rotation.

After performing the translation and/or rotation, anatomical display module 406 proceeds to determine whether the error is greater than the maximum deviation amount (1208). Anatomical display module 406 continues to iteratively select and perform the translation and/or rotation along the first movement distance that causes the greatest reduction in error until the error amount falls below the current deviation threshold (1210). In some examples, this deviation threshold may start at 1 mm. Then, anatomical display module reduces, such as halving, the deviation threshold and the movement amount to 0.5 mm (1220). Again, the anatomical display module 406 continues to iteratively select and perform the translation and/or rotation along the movement amount that causes the greatest reduction in error until the error amount falls below the deviation threshold of 0.5 mm (1210). The anatomical display module continues to reduce the deviation threshold and movement and iteratively translate and rotate the atlas-defined structure 602A by the movement amount until the error amount falls below the maximum deviation set by the clinician (1208). In one example, the maximum deviation is 0.1 mm. However, as described above, the techniques of the disclosure are suitable for many different maximum deviation amounts, and in some examples, the maximum deviation is set to 1 mm, 0.3 mm, 1 μm, or 0.1 μm. Once the error between the respective points of the annotation and atlas-defined structure is below the maximum deviation ("YES" branch of block 1208), anatomical display module 406 then controls user interface 402 to display the adjusted anatomical structures at the most recent position over the anatomical region (1222).

The techniques described in this disclosure may be implemented, at least in part, in hardware, software, firmware or any combination thereof. For example, various aspects of the described techniques may be implemented within one or more processors, including one or more microprocessors, digital signal processors (DSPs), application specific integrated circuits (ASICs), field programmable gate arrays (FPGAs), or any other equivalent integrated or discrete logic circuitry, as well as any combinations of such components. The term "processor" or "processing circuitry" may generally refer to any of the foregoing logic circuitry, alone or in combination with other logic circuitry, or any other equivalent circuitry. A control unit comprising hardware may also perform one or more of the techniques of this disclosure.

Such hardware, software, and firmware may be implemented within the same device or within separate devices to support the various operations and functions described in this disclosure. In addition, any of the described units, modules or components may be implemented together or separately as discrete but interoperable logic devices. Depiction of different features as modules or units is intended to highlight different functional aspects and does not necessarily imply that such modules or units must be realized by separate hardware or software components. Rather, functionality associated with one or more modules or units may be performed by separate hardware or software components, or integrated within common or separate hardware or software components. Each of the modules described herein may be or include processing circuitry or other electrical circuitry configured to perform the functions attributed to the specific module that is described.

The techniques described in this disclosure may also be embodied or encoded in a computer-readable medium, such as a computer-readable storage medium, containing instructions. Instructions embedded or encoded in a computer-readable storage medium may cause a programmable processor, or other processor, to perform the method, e.g., when the instructions are executed. Computer readable storage media may include random access memory (RAM), read only memory (ROM), programmable read only memory (PROM), erasable programmable read only memory (EPROM), electronically erasable programmable read only memory (EEPROM), flash memory, a hard disk, a CD-ROM, a floppy disk, a cassette, magnetic media, optical media, or other computer readable media.

Various examples have been described. These and other examples are within the scope of the following claims.

What is claimed is:

1. A method comprising:
    generating, by one or more processors and for display at a user interface, a representation of an anatomical region of a patient;
    generating, by the one or more processors and for display at the user interface, a representation of one or more atlas-defined anatomical structures at a first position over the representation of the anatomical region of the patient;
    receiving, by the one or more processors, a user annotation that defines an adjustment to at least one atlas-defined anatomical structure of the one or more atlas-defined anatomical structures relative to the representation of the anatomical region of the patient;
    determining, by the one or more processors and based on the adjustment defined by the user annotation, one or more adjustments of the representation of the one or more atlas-defined anatomical structures by one or more movement amounts;
    selecting, by the one or more processors, one of the one or more adjustments that decreases a distance between the representation of the one or more atlas-defined anatomical structures and the annotation by a greatest amount;
    performing, by the one or more processors, the one of the one or more adjustments that decreases the distance between the representation of the one or more atlas-defined anatomical structures and the annotation by the greatest amount to move the representation of the one or more atlas-defined anatomical structures to a second position over the representation of the anatomical region of the patient; and
    controlling, by the one or more processors, the user interface to display the representation of the one or more atlas-defined anatomical structures at the second position over the representation of the anatomical region of the patient.

2. The method of claim 1, wherein:
    generating the representation of the anatomical region of the patient comprises:
        generating a coronal view of the anatomical region;
        generating a sagittal view of the anatomical region; and
        generating an axial view of the anatomical region; and
    generating the representation of the one or more atlas-defined anatomical structures at the first position over the representation of the anatomical region of the patient comprises:
        generating a coronal view of the one or more atlas-defined anatomical structures at the first position over the coronal view of the anatomical region;
        generating a sagittal view of the one or more atlas-defined anatomical structures at the first position over the sagittal view of the anatomical region; and
        generating an axial view of the one or more atlas-defined anatomical structures at the first position over the axial view of the anatomical region.

3. The method of claim 2, wherein receiving the user annotation comprises receiving the user annotation with respect to at least one of the coronal view of the anatomical region, the sagittal view of the anatomical region, or the axial view of the anatomical region.

4. The method of claim 1, wherein receiving the user annotation comprises receiving an adjustment to one or more control points, each control point of the one or more control points defining a position of at least one atlas-defined anatomical structure of the one or more atlas-defined anatomical structures with respect to the representation of the anatomical region of the patient.

5. The method of claim 1, wherein:
receiving the user annotation comprises receiving, by the user interface, user input dragging a portion of at least one of the one or more atlas-defined anatomical structures from a first location with respect to the representation of the anatomical region of the patient to a second location with respect to the representation of the anatomical region of the patient; and
determining, based on the adjustment defined by the user annotation, the one or more adjustments of the representation of the one or more atlas-defined anatomical structures by the one or more movement amounts comprises determining, based on the dragging, the one or more adjustments of the representation of the one or more atlas-defined anatomical structures by the one or more movement amounts.

6. The method of claim 1, wherein determining, based on the adjustment defined by the user annotation, the one or more adjustments, selecting, the one of the one or more adjustments, and performing the one of the one or more adjustments comprises:
determining, by the one or more processors, one or more translations of the representation of the one or more atlas-defined anatomical structures by a first movement amount;
selecting, by the one or more processors, one of the one or more translations that decreases a distance between the representation of the one or more atlas-defined anatomical structures and the annotation by a greatest amount;
performing, by the one or more processors, the one of the one or more translations that decreases the distance between the representation of the one or more atlas-defined anatomical structures and the annotation by the greatest amount;
determining, by the one or more processors, one or more rotations of the representation of the one or more atlas-defined anatomical structures by the first movement amount;
selecting, by the one or more processors, one of the one or more rotations that decreases a distance between the representation of the one or more atlas-defined anatomical structures and the annotation by a greatest amount; and
performing, by the one or more processors, the one of the one or more rotations that decreases the distance between the representation of the one or more atlas-defined anatomical structures and the annotation by the greatest amount.

7. The method of claim 1, wherein determining, based on the adjustment defined by the user annotation, the one or more adjustments, selecting, the one of the one or more adjustments, and performing the one of the one or more adjustments comprises:
until the one or more processors determine that a distance between the representation of the one or more atlas-defined anatomical structures and the annotation is less than a predetermined tolerance:
determining, by the one or more processors, whether the distance between the representation of the one or more atlas-defined anatomical structures and the annotation is less than the predetermined tolerance; and
responsive to determining that the distance is not less than the predetermined tolerance:
determining, by the one or more processors, one or more translations of the representation of the one or more atlas-defined anatomical structures by a first movement amount;
selecting, by the one or more processors, one of the one or more translations that decreases a distance between the representation of the one or more atlas-defined anatomical structures and the annotation by a greatest amount;
performing, by the one or more processors, the one of the one or more translations that decreases the distance between the representation of the one or more atlas-defined anatomical structures and the annotation by the greatest amount;
determining, by the one or more processors, one or more rotations of the representation of the one or more atlas-defined anatomical structures by the first movement amount;
selecting, by the one or more processors, one of the one or more rotations that decreases a distance between the representation of the one or more atlas-defined anatomical structures and the annotation by a greatest amount; and
performing, by the one or more processors, the one of the one or more rotations that decreases the distance between the representation of the one or more atlas-defined anatomical structures and the annotation by the greatest amount.

8. The method of claim 1, further comprising displaying, by a display device, a user interface that includes:
the representation of the anatomical region of the patient;
the representation of the one or more atlas-defined structures; and
the user annotation.

9. The method of claim 1, wherein:
the anatomical region is generated based on one or more images of a brain of the patient, and
the atlas-defined anatomical structures are structures defined by a brain atlas.

10. The method of claim 1, further comprising controlling, by the one or more processors, delivery of electrical stimulation based on a location of an electrical stimulation lead with respect to the second position of the representation of the one or more atlas-defined anatomical structures over the representation of the anatomical region of the patient.

11. The method of claim 1,
wherein determining the one or more adjustments of the representation of the one or more atlas-defined anatomical structures by one or more movement amounts comprises determining one or more translations of the representation of the one or more atlas-defined anatomical structures by one or more movement amounts;
wherein selecting the one of the one or more adjustments that decreases a distance between the representation of the one or more atlas-defined anatomical structures and the annotation by a greatest amount comprises selecting the one of the one or more translations that decreases a distance between the representation of the one or more atlas-defined anatomical structures and the annotation by a greatest amount; and wherein performing the one of the one or more adjustments that decreases the distance between the representation of the one or more atlas-defined anatomical structures and the annotation by the greatest amount comprises performing the one of the one or more translations that decreases the distance between the representation of the one or more atlas-defined anatomical structures and the annotation by the greatest amount.

12. The method of claim 1,
wherein determining the one or more adjustments of the representation of the one or more atlas-defined anatomical structures by one or more movement amounts comprises determining one or more rotations of the representation of the one or more atlas-defined anatomical structures by one or more movement amounts;
wherein selecting the one of the one or more adjustments that decreases a distance between the representation of the one or more atlas-defined anatomical structures and the annotation by a greatest amount comprises selecting the one of the one or more rotations that decreases a distance between the representation of the one or more atlas-defined anatomical structures and the annotation by a greatest amount; and
wherein performing the one of the one or more adjustments that decreases the distance between the representation of the one or more atlas-defined anatomical structures and the annotation by the greatest amount comprises performing the one of the one or more rotations that decreases the distance between the representation of the one or more atlas-defined anatomical structures and the annotation by the greatest amount.

13. A system, comprising:
processing circuitry configured to:
    generate, for display at a user interface, a representation of an anatomical region of a patient;
    generate, for display at the user interface, a representation of one or more atlas-defined anatomical structures at a first position over the representation of the anatomical region of the patient;
    receive a user annotation that defines an adjustment to at least one atlas-defined anatomical structure of the one or more atlas-defined anatomical structures relative to the representation of the anatomical region of the patient;
    determine, based on the adjustment defined by the user annotation, one or more adjustments of the representation of the one or more atlas-defined anatomical structures by one or more movement amounts;
    select one of the one or more adjustments that decreases a distance between the representation of the one or more atlas-defined anatomical structures and the annotation by a greatest amount;
    perform the one of the one or more adjustments that decreases the distance between the representation of the one or more atlas-defined anatomical structures and the annotation by the greatest amount to move the representation of the one or more atlas-defined anatomical structures to a second position over the representation of the anatomical region of the patient; and
    control the user interface to display the representation of the one or more atlas-defined anatomical structures at the second position over the representation of the anatomical region of the patient.

14. The system of claim 13, wherein the processing circuitry is configured to generate the representation of the anatomical region of the patient by:
    generating a coronal view of the anatomical region;
    generating a sagittal view of the anatomical region; and
    generating an axial view of the anatomical region; and
    generate the representation of the one or more atlas-defined anatomical structures at the first position over the representation of the anatomical region of the patient by:
    generating a coronal view of the one or more atlas-defined anatomical structures at the first position over the coronal view of the anatomical region;
    generating a sagittal view of the one or more atlas-defined anatomical structures at the first position over the sagittal view of the anatomical region; and
    generating an axial view of the one or more atlas-defined anatomical structures at the first position over the axial view of the anatomical region.

15. The system of claim 14, wherein the processing circuitry is configured to receive the user annotation with respect to at least one of the coronal view of the anatomical region, the sagittal view of the anatomical region, or the axial view of the anatomical region.

16. The system of claim 13, wherein the processing circuitry is configured to receive an adjustment to one or more control points, each control point of the one or more control points defining a position of at least one atlas-defined anatomical structure of the one or more atlas-defined anatomical structures with respect to the representation of the anatomical region of the patient.

17. The system of claim 13, further comprising a user interface configured to receive user input dragging a portion of at least one of the one or more atlas-defined anatomical structures from a first location with respect to the representation of the anatomical region of the patient to a second location with respect to the representation of the anatomical region of the patient, and
    wherein the processing circuitry is configured to determine, based on the adjustment defined by the user annotation, the one or more adjustments of the representation of the one or more atlas-defined anatomical structures by the one or more movement by determining, based on the dragging, the one or more adjustments of the representation of the one or more atlas-defined anatomical structures by the one or more movement amounts.

18. The system of claim 13, wherein the processing circuitry is configured to determine, based on the adjustment defined by the user annotation, the one or more adjustments, select the one of the one or more adjustments, and perform the one of the one or more adjustments by:
    determining one or more translations of the representation of the one or more atlas-defined anatomical structures by a first movement amount;
    selecting one of the one or more translations that decreases a distance between the representation of the one or more atlas-defined anatomical structures and the annotation by a greatest amount;
    performing the one of the one or more translations that decreases the distance between the representation of the one or more atlas-defined anatomical structures and the annotation by the greatest amount;
    determining one or more rotations of the representation of the one or more atlas-defined anatomical structures by the first movement amount;

selecting one of the one or more rotations that decreases a distance between the representation of the one or more atlas-defined anatomical structures and the annotation by a greatest amount; and
performing the one of the one or more rotations that decreases the distance between the representation of the one or more atlas-defined anatomical structures and the annotation by the greatest amount.

19. The system of claim 13, wherein the processing circuitry is configured to determine, based on the adjustment defined by the user annotation, the one or more adjustments, select the one of the one or more adjustments, and perform the one of the one or more adjustments by:
   until the processing circuitry determines that a distance between the representation of the one or more atlas-defined anatomical structures and the annotation is less than a predetermined tolerance:
      determining whether the distance between the representation of the one or more atlas-defined anatomical structures and the annotation is less than the predetermined tolerance; and
      responsive to determining that the distance is not less than the predetermined tolerance:
         determining one or more translations of the representation of the one or more atlas-defined anatomical structures by a first movement amount;
         selecting one of the one or more translations that decreases a distance between the representation of the one or more atlas-defined anatomical structures and the annotation by a greatest amount;
         performing the one of the one or more translations that decreases the distance between the representation of the one or more atlas-defined anatomical structures and the annotation by the greatest amount;
         determining one or more rotations of the representation of the one or more atlas-defined anatomical structures by the first movement amount;
         selecting one of the one or more rotations that decreases a distance between the representation of the one or more atlas-defined anatomical structures and the annotation by a greatest amount; and
         performing the one of the one or more rotations that decreases the distance between the representation of the one or more atlas-defined anatomical structures and the annotation by the greatest amount.

20. The system of claim 13, further comprising a display device configured to display a user interface that includes:
   the representation of the anatomical region of the patient;
   the representation of the one or more atlas-defined structures; and
   the user annotation.

21. The system of claim 13, wherein:
   the anatomical region is generated based on one or more images of a brain of the patient, and
   the atlas-defined anatomical structures are structures defined by a brain atlas.

22. The system of claim 13, wherein the processing circuitry is configured to control delivery of electrical stimulation based on a location of an electrical stimulation lead with respect to the second position of the representation of the one or more atlas-defined anatomical structures over the representation of the anatomical region of the patient.

23. The system of claim 13,
   wherein to determine the one or more adjustments of the representation of the one or more atlas-defined anatomical structures by one or more movement amounts, the processing circuitry is configured to determine one or more translations of the representation of the one or more atlas-defined anatomical structures by one or more movement amounts;
   wherein to select the one of the one or more adjustments that decreases a distance between the representation of the one or more atlas-defined anatomical structures and the annotation by a greatest amount, the processing circuitry is configured to select the one of the one or more translations that decreases a distance between the representation of the one or more atlas-defined anatomical structures and the annotation by a greatest amount; and
   wherein to perform the one of the one or more adjustments that decreases the distance between the representation of the one or more atlas-defined anatomical structures and the annotation by the greatest amount, the processing circuitry is configured to perform the one of the one or more translations that decreases the distance between the representation of the one or more atlas-defined anatomical structures and the annotation by the greatest amount.

24. The system of claim 13,
   wherein to determine the one or more adjustments of the representation of the one or more atlas-defined anatomical structures by one or more movement amounts, the processing circuitry is configured to determine one or more rotations of the representation of the one or more atlas-defined anatomical structures by one or more movement amounts;
   wherein to select the one of the one or more adjustments that decreases a distance between the representation of the one or more atlas-defined anatomical structures and the annotation by a greatest amount, the processing circuitry is configured to select the one of the one or more rotations that decreases a distance between the representation of the one or more atlas-defined anatomical structures and the annotation by a greatest amount; and
   wherein to perform the one of the one or more adjustments that decreases the distance between the representation of the one or more atlas-defined anatomical structures and the annotation by the greatest amount, the processing circuitry is configured to perform the one of the one or more rotations that decreases the distance between the representation of the one or more atlas-defined anatomical structures and the annotation by the greatest amount.

25. A non-transitory computer readable medium comprising instructions that, when executed, cause at least one processor to:
   generate, for display at a user interface, a representation of an anatomical region of a patient;
   generate, for display at the user interface, a representation of one or more atlas-defined anatomical structures at a first position over the representation of the anatomical region of the patient;
   receive a user annotation that defines an adjustment to at least one atlas-defined anatomical structure of the one or more atlas-defined anatomical structures relative to the representation of the anatomical region of the patient;
   determine, based on the adjustment defined by the user annotation, one or more adjustments of the representation of the one or more atlas-defined anatomical structures by one or more movement amounts;

select one of the one or more adjustments that decreases a distance between the representation of the one or more atlas-defined anatomical structures and the annotation by a greatest amount;

perform the one of the one or more adjustments that decreases the distance between the representation of the one or more atlas-defined anatomical structures and the annotation by the greatest amount to move the representation of the one or more atlas-defined anatomical structures to a second position over the representation of the anatomical region of the patient; and control the user interface to display the representation of the one or more atlas-defined anatomical structures at the second position over the representation of the anatomical region of the patient.

* * * * *